(12) United States Patent
Dixit et al.

(10) Patent No.: US 8,354,428 B2
(45) Date of Patent: Jan. 15, 2013

US008354428B2

(54) SOLID STATE FORMS OF LAQUINIMOD AND ITS SODIUM SALT

(75) Inventors: Girish Dixit, Uttar Pradesh (IN); Krishnadatt Sharma, Maharashtra (IN); Nitin Sharadchandra Pradhan, Maharashtra (IN); Jon Valgeirsson, Hafnarfjörður (IS)

(73) Assignee: Actavis Group PTC EHF (IS)

( * ) Notice: Subject to any disclaimer, the term of this patent is extended or adjusted under 35 U.S.C. 154(b) by 98 days.

(21) Appl. No.: 13/001,715

(22) PCT Filed: Jun. 30, 2009

(86) PCT No.: PCT/IB2009/006560
§ 371 (c)(1),
(2), (4) Date: Apr. 4, 2011

(87) PCT Pub. No.: WO2010/001257
PCT Pub. Date: Jan. 7, 2010

(65) Prior Publication Data
US 2011/0171270 A1 Jul. 14, 2011

(30) Foreign Application Priority Data
Jul. 1, 2008 (IN) .......................... 1602/CHE/2008

(51) Int. Cl.
*A61K 31/04* (2006.01)
*C07D 215/38* (2006.01)

(52) U.S. Cl. ...................................... 514/312; 546/155

(58) Field of Classification Search .................. 514/312; 546/155
See application file for complete search history.

(56) References Cited

U.S. PATENT DOCUMENTS

| 6,077,851 | A * | 6/2000 | Bjork et al. .................... 514/312 |
| 6,875,869 | B2 * | 4/2005 | Jansson ........................... 546/90 |
| 7,589,208 | B2 * | 9/2009 | Jansson et al. ................. 546/155 |
| 2005/0192315 | A1 * | 9/2005 | Jansson et al. ................. 514/312 |
| 2009/0232889 | A1 * | 9/2009 | Jansson et al. ................. 424/465 |

FOREIGN PATENT DOCUMENTS
WO 2007047863 A2 4/2007

OTHER PUBLICATIONS

Jansson, et al.; "Synthesis and Reactivity of Laquinimod, a Quinoline-3-Carboxamide: Intramolecular Transfer of the Enol Proton to a Nitrogen Atom as a Plausible Mechanism for Ketene Formation"; J. Org. Chem; 71; pp. 1658-1667; (2006).
Jonsson, et al.; "Synthesis and Biological Evaluation of New 1,2-Dihydro-4-Hydroxy-2-Oxo-3-Quinolinecarboxamides for Treatment of Autoimmune Disorders: Structure-Activity Relationship"; J. Med. Chem; 47; pp. 2075-2088; (2004).
International Search Report; International Application No. PCT/IB2009/006560; International Filing Date Jun. 30, 2009; Applicant's File Reference; Date of Mailing Dec. 28, 2010; 7 pages.
International Written Opinion; International Application No. PCT/IB2009/006560; International Filing Date Jun. 30, 2009; Applicant's File Reference; Date of Mailing Dec. 28, 2010; 10 pages.
Konno, Tsutomu; "Physical and Chemical Changes of Medicinals in Mixtures with Adsorbents in the Solid State. IV. Study on Reduced-Pressure Mixing for Practical Use of Amorphous Mixtures of Flufenamic Acid"; Chem. Pharm. Bull.; 38; pp. 2003-2007; (1990).

* cited by examiner

*Primary Examiner* — D M Seaman
(74) *Attorney, Agent, or Firm* — Cantor Colburn LLP

(57) ABSTRACT

Provided herein is a novel crystalline form of laquinimod, process for the preparation, pharmaceutical compositions, and method of treating thereof. Provided also herein are novel amorphous and polymorphic forms of laquinimod sodium, process for the preparation, pharmaceutical compositions, and method of treating thereof.

18 Claims, 9 Drawing Sheets

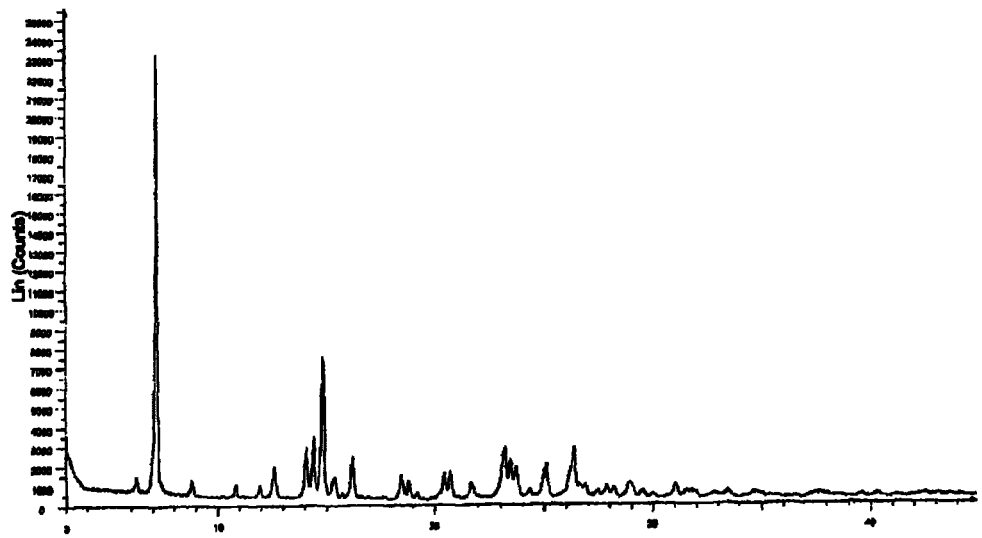
Figure 1: Powder X-ray diffraction (XRD) pattern of Laquinimod crystalline Form A
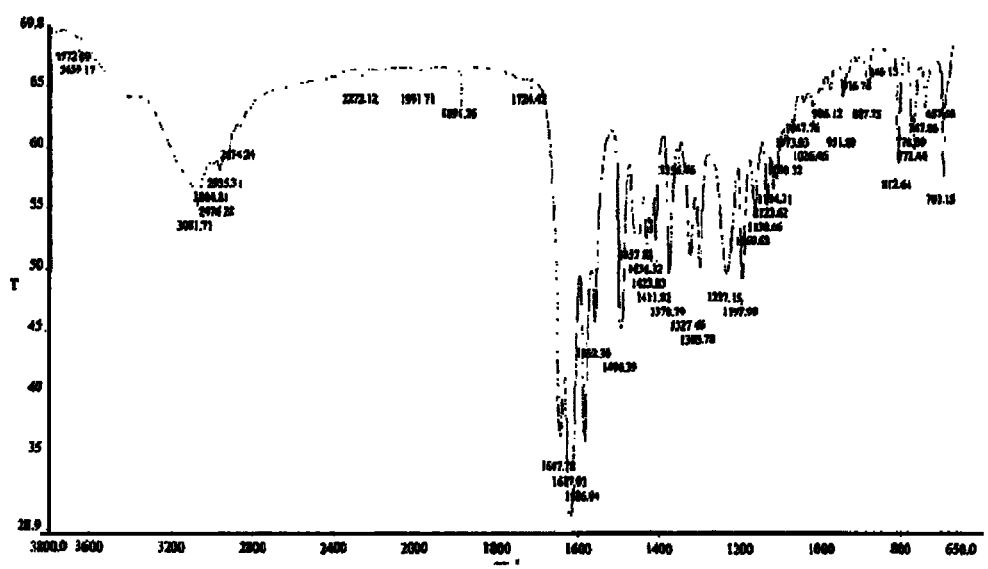
Figure 2: Infra red (IR) spectrum of Laquinimod crystalline Form A

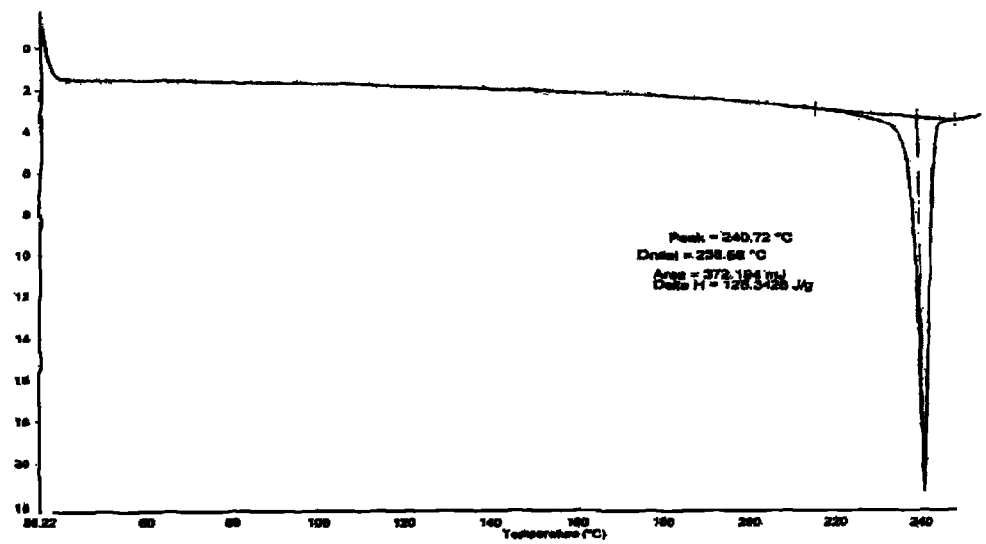
Figure 3: Differential scanning calorimetric (DSC) thermogram of Laquinimod crystalline Form A
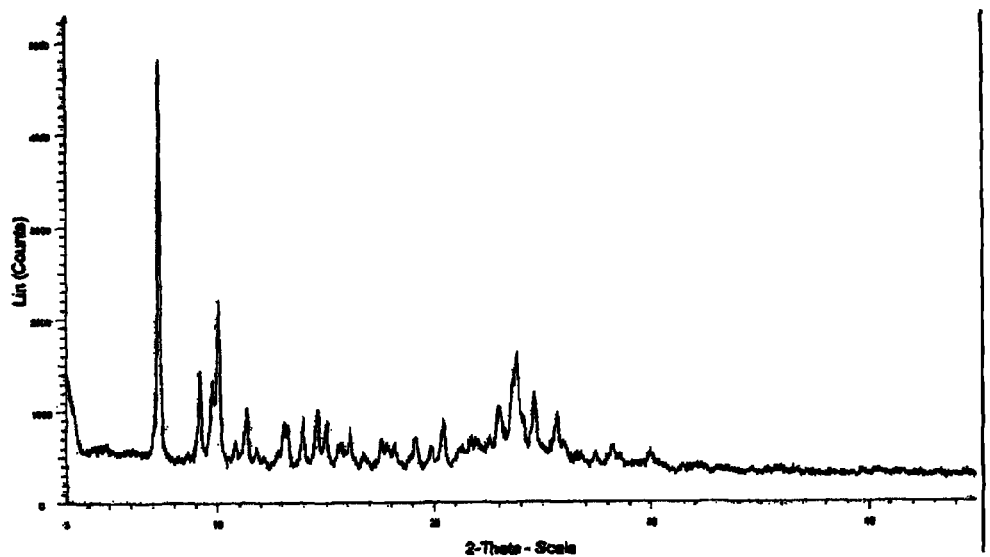
Figure 4: Powder X-ray diffraction (XRD) pattern of Laquinimod sodium crystalline Form A1

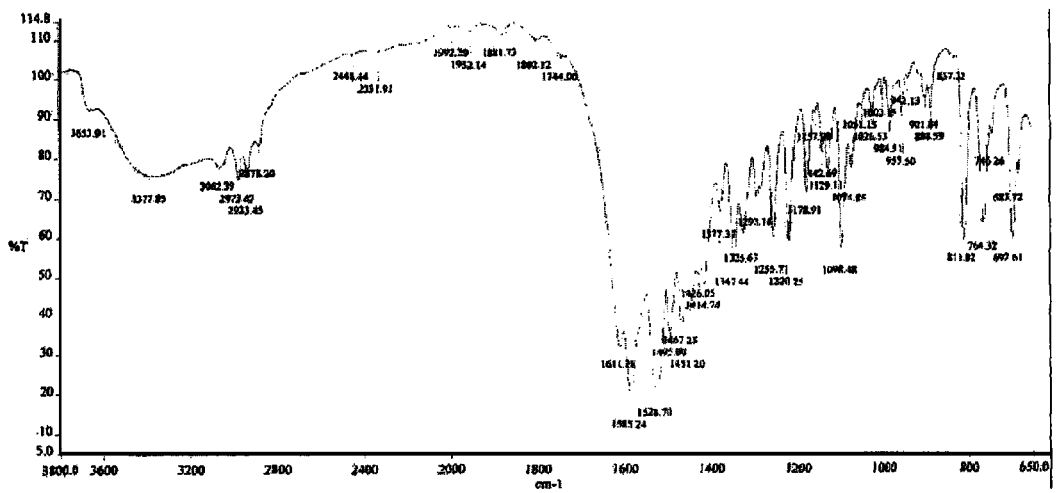
Figure 5: Infra red (IR) spectrum of Laquinimod sodium crystalline Form A1
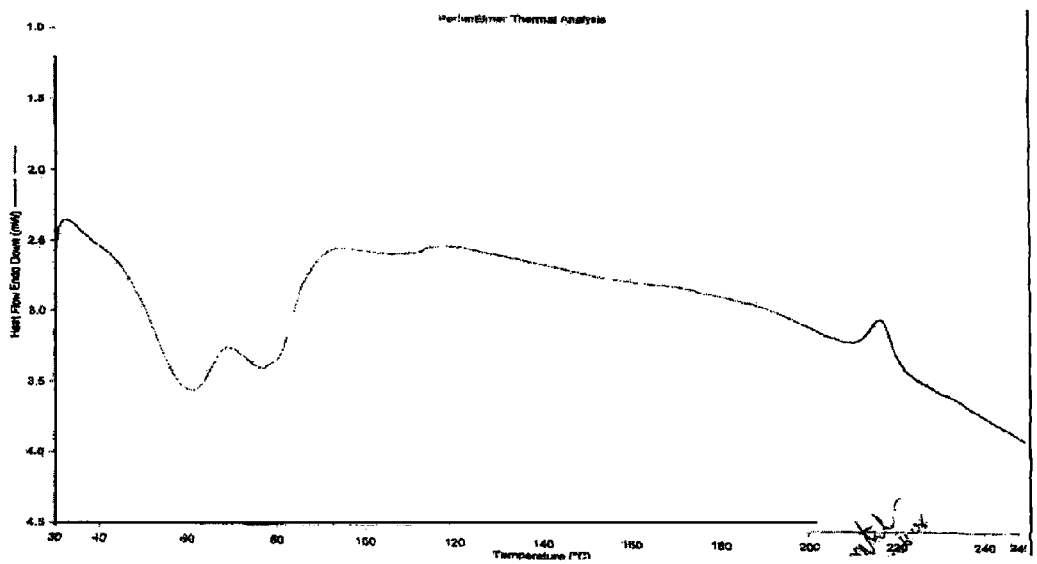
Figure 6: Differential scanning calorimetric (DSC) thermogram of Laquinimod sodium crystalline Form A1

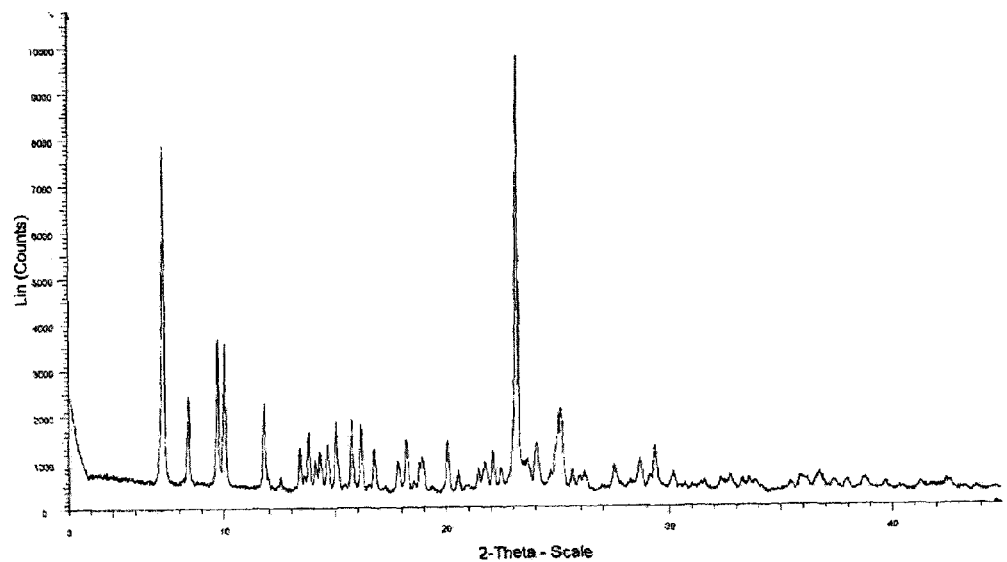
Figure 7: Powder X-ray diffraction (XRD) pattern of Laquinimod sodium crystalline Form A2
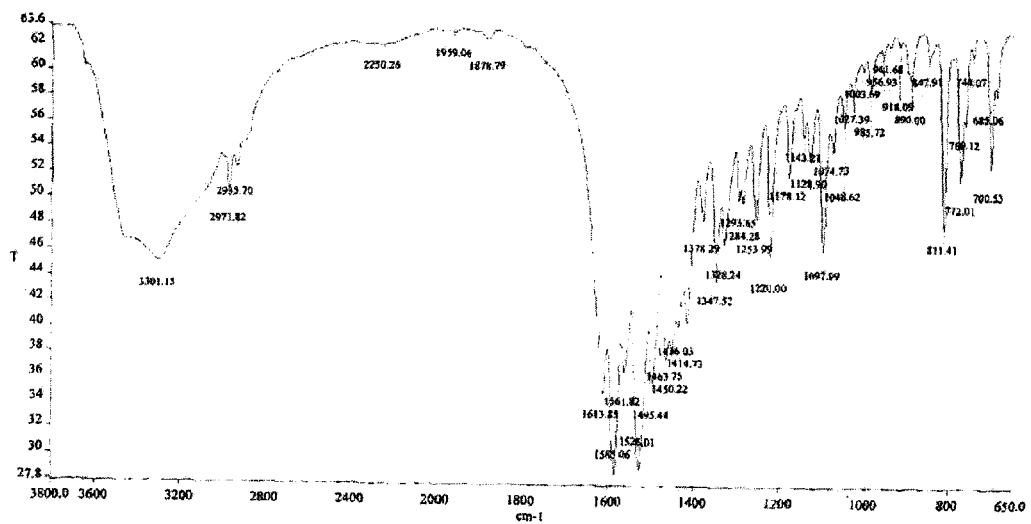
Figure 8: Infra red (IR) spectrum of Laquinimod sodium crystalline Form A2

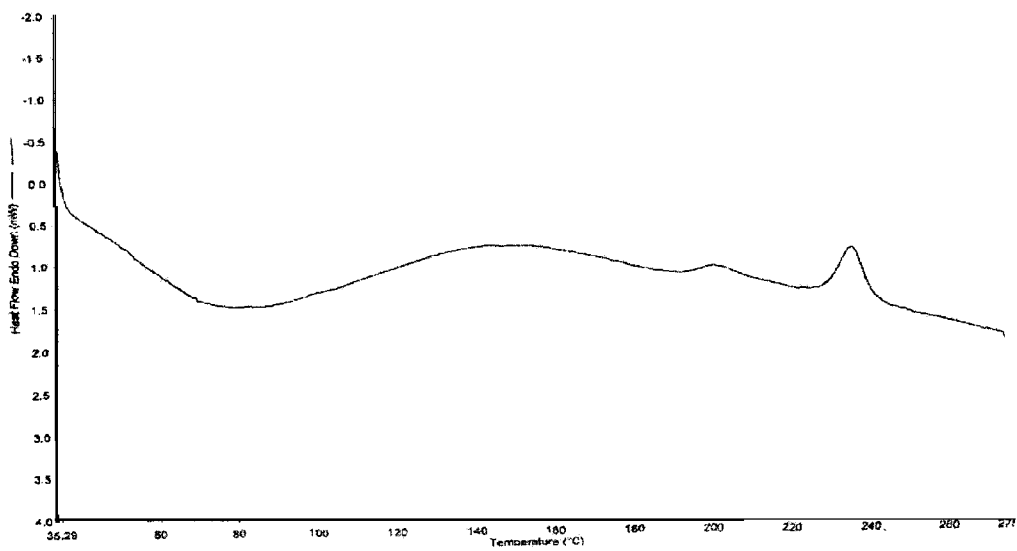
Figure 9: Differential scanning calorimetric (DSC) thermogram of Laquinimod sodium crystalline Form A2
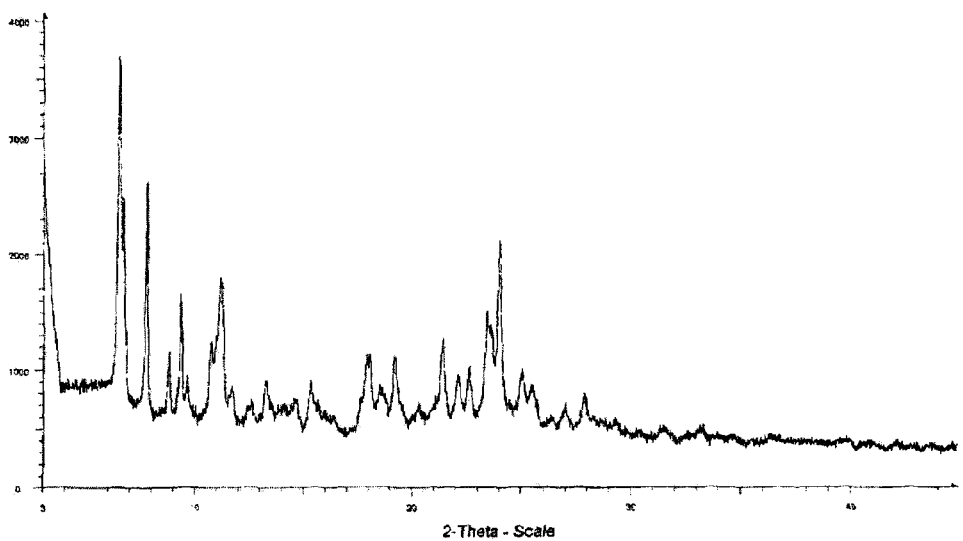
Figure 10: Powder X-ray diffraction (XRD) pattern of Laquinimod sodium crystalline Form A3

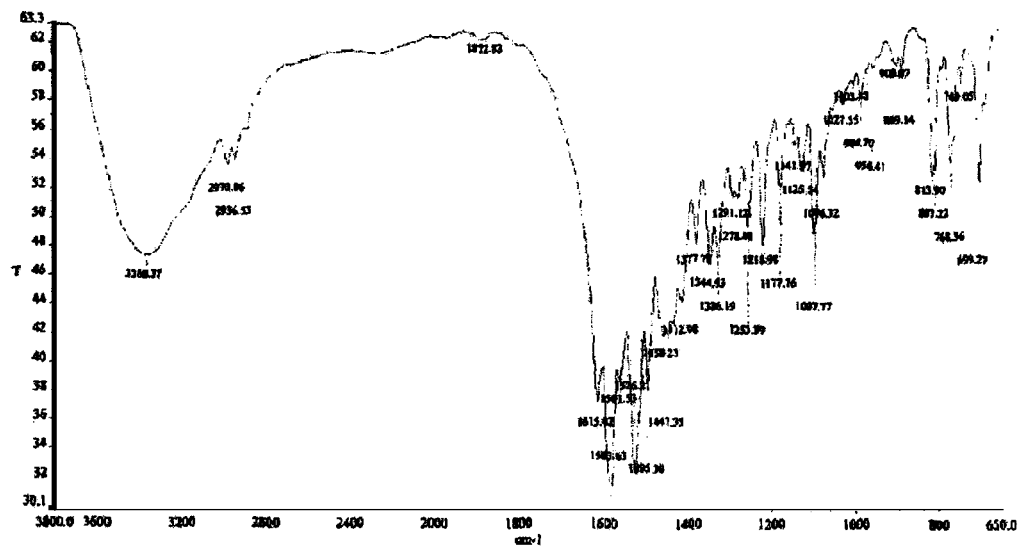
Figure 11: Infra red (IR) spectrum of Laquinimod sodium crystalline Form A3
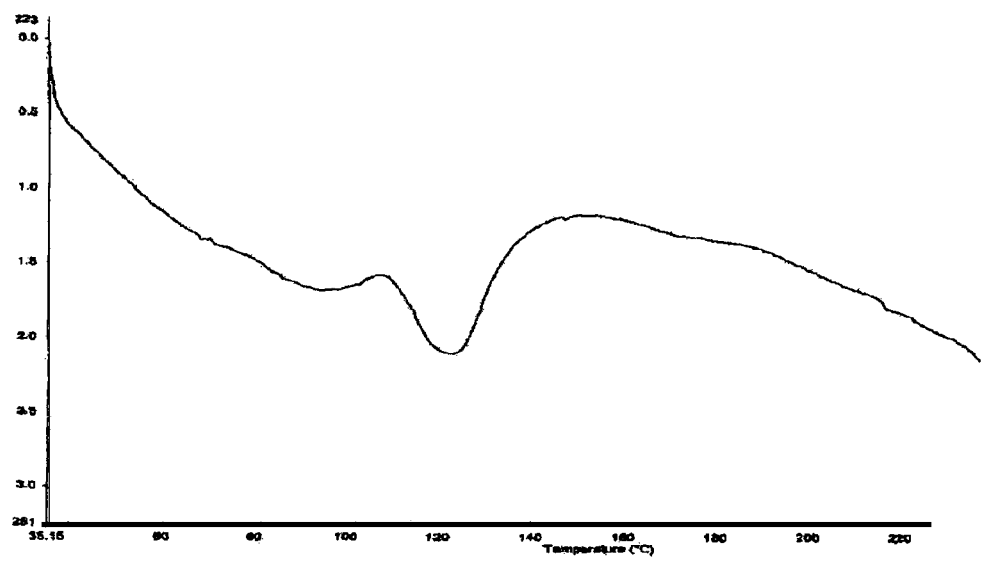
Figure 12: Differential scanning calorimetric (DSC) thermogram of Laquinimod sodium crystalline Form A3

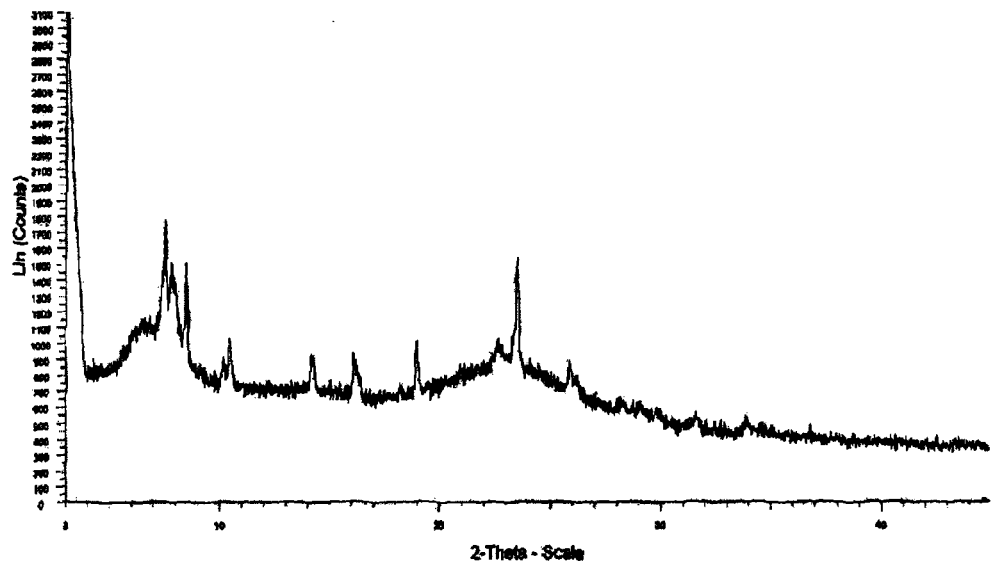
Figure 13: Powder X-ray diffraction (XRD) pattern of Laquinimod sodium crystalline Form A4
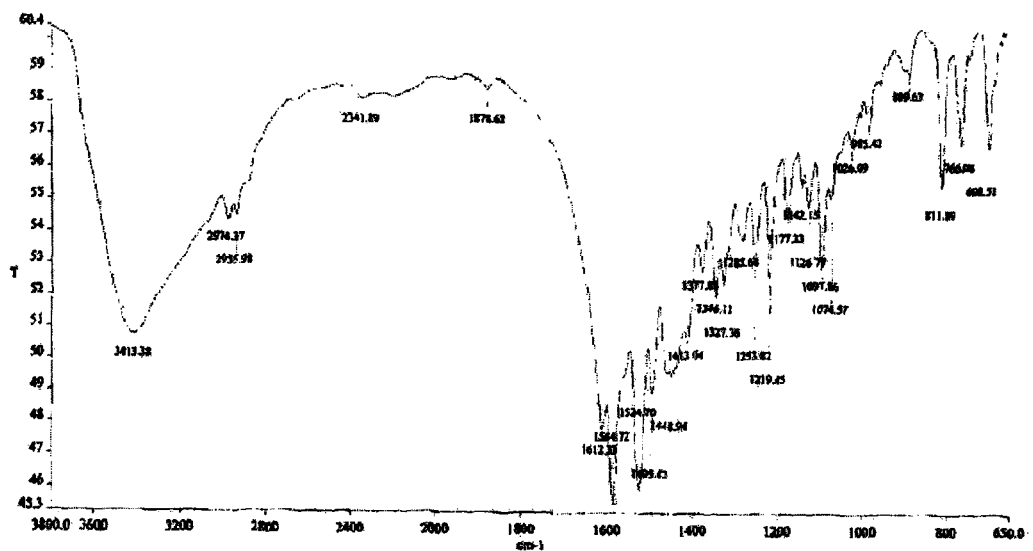
Figure 14: Infra red (IR) spectrum of Laquinimod sodium crystalline Form A4

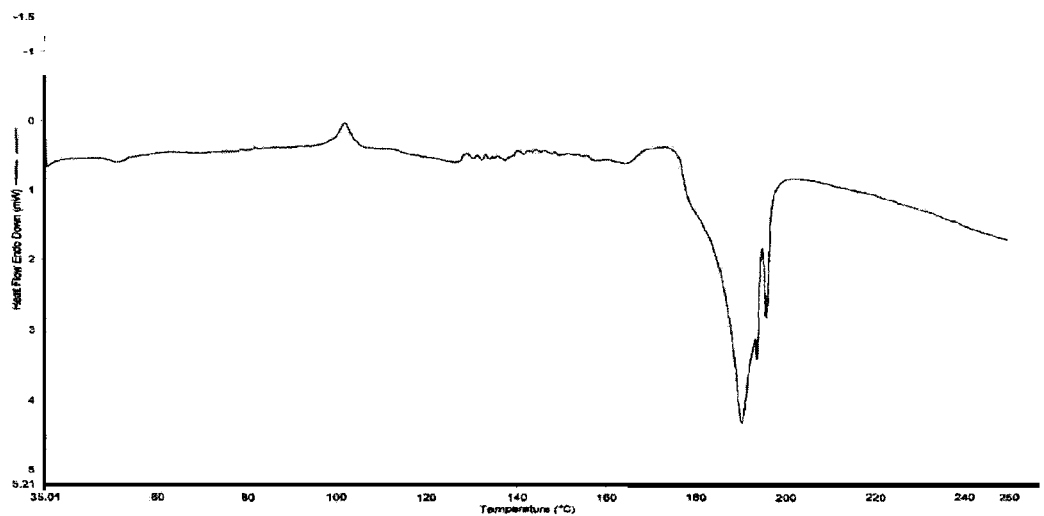
Figure 15: Differential scanning calorimetric (DSC) thermogram of Laquinimod sodium crystalline Form A4
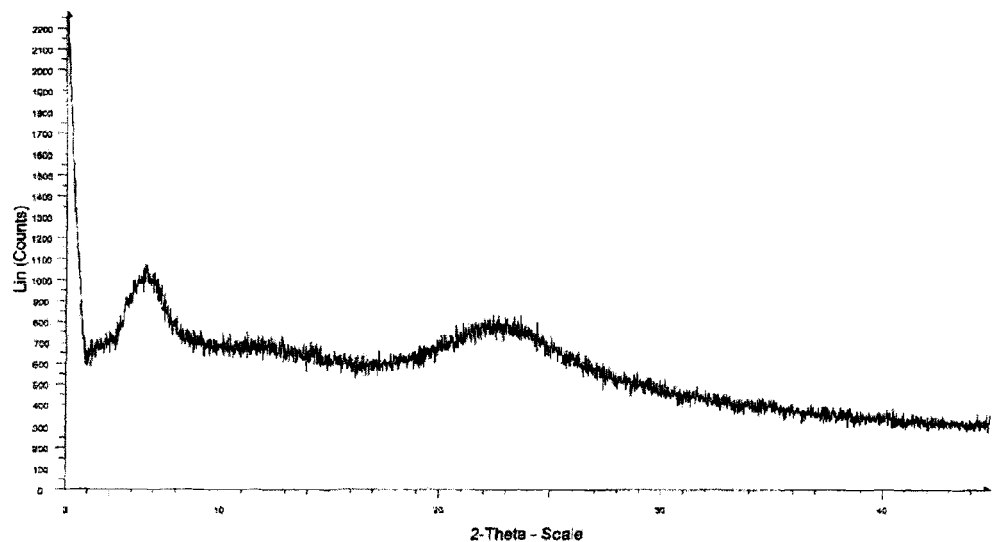
Figure 16: Powder X-ray diffraction (XRD) pattern of amorphous Laquinimod sodium

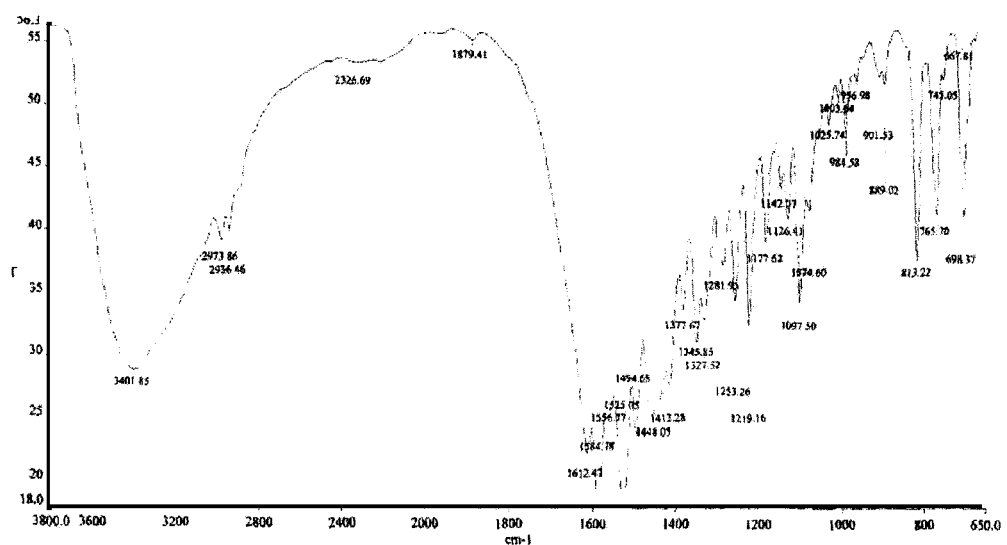
Figure 17: Infra red (IR) spectrum of amorphous laquinimod sodium.

US 8,354,428 B2

SOLID STATE FORMS OF LAQUINIMOD AND ITS SODIUM SALT

CROSS-REFERENCE TO RELATED APPLICATIONS

This application is a 371 of PCT/IB2009/006560, filed Jun. 30, 2009, which claims the benefit of priority to Indian provisional application No. 1602/CHE/2008, filed on Jul. 1, 2008; under provisions of 35 U.S.C. 119 and the International Convention for the protection of Industrial Property, which are incorporated herein by reference in their entirety.

FIELD OF THE DISCLOSURE

The present disclosure relates to a novel crystalline form of laquinimod, process for the preparation, pharmaceutical compositions, and method of treating thereof. The present disclosure further relates to novel solid state forms of laquinimod sodium, process for the preparation, pharmaceutical compositions, and method of treating thereof.

BACKGROUND

U.S. Pat. No. 6,077,851 discloses a variety of quinoline-3-carboxamide derivatives and their salts, processes for their preparation, pharmaceutical compositions comprising the derivatives, and method of use thereof. These compounds are useful for clinical treatment of diseases resulting from autoimmunity such as multiple sclerosis, insulin-dependent diabetes mellitus, systemic lupus erythematosus, rheumatoid arthritis, inflammatory bowel disease and psoriasis and, furthermore, diseases where pathologic inflammation plays a major role, such as asthma, atherosclerosis, stroke and Alzheimer's disease. Of these compounds, N-ethyl-N-phenyl-1,2-dihydro-4-hydroxy-5-chloro-1-methyl-2-oxoquinoline-3-carboxamide is important, since it is well-known as a pharmaceutically active substance under the name of Laquinimod. Laquinimod is a promising immunomodulatory agent and useful for the treatment of multiple sclerosis and its manifestations. Laquinimod is represented by the following structural formula:

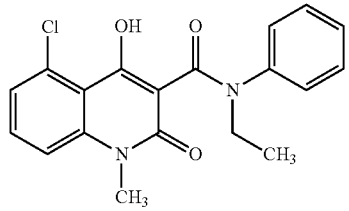 [SMILES: CCN(C(=O)c1c(O)c2c(Cl)cccc2n(C)c1=O)c1ccccc1]

Processes for the preparation of laquinimod and its sodium salt are disclosed in U.S. Pat. Nos. 6,077,851 and 6,875,869.

U.S. Pat. No. 6,077,851 (hereinafter referred to as the '851 patent) describes several synthetic routes for preparing laquinimod. According to a first synthetic process, laquinimod is prepared by the reaction of 1,2-dihydro-4-hydroxy-5-chloro-1-methyl-2-oxo-quinoline-3-carboxylic acid ethyl ester with N-ethylaniline in a suitable solvent such as toluene, xylene and the like, to produce a reaction mass containing laquinimod, followed by distillation of ethanol formed during the reaction and then subjected to usual work up to produce laquinimod, which is then converted into its sodium salt.

According to a second synthetic process as described in the '851 patent, laquinimod is prepared by the reaction of 5-chloro isatoic anhydride with N-ethyl-N-phenylcarbamoyl acetic acid ethyl ester in the presence of methyl iodide and a strong base such as sodium hydride in a suitable solvent such as N,N-dimethylacetamide.

According to a third synthetic process as described in the '851 patent, laquinimod is prepared by the reaction of 1,2-dihydro-4-hydroxy-5-chloro-1-methyl-2-oxo-quinoline-3-carboxylic acid with N-ethylaniline using coupling reagents such as carbodiimides and thionyl chloride in the presence of triethylamine to produce laquinimod.

Laquinimod obtained by the processes described in the '851 patent is further recrystallized from methanol to produce laquinimod with greater than 95% purity.

The '851 patent makes no reference to the existence of specific polymorphic forms of laquinimod sodium. According to the embodiments exemplified, the product is obtained by suspending laquinimod in ethanol, adding 5M sodium hydroxide solution to the suspension by adjusting the pH to 8-12, stirring the reaction mixture for 30 minutes at ambient temperature and recovering the precipitated laquinimod sodium.

U.S. Pat. No. 6,875,869 (hereinafter referred to as the '869 patent) describes an improved process for the preparation of laquinimod comprising reacting 1,2-dihydro-4-hydroxy-5-chloro-1-methyl-2-oxo-quinoline-3-carboxylic acid methyl ester with N-ethylaniline in the presence of a solvent selected from straight or branched alkanes and cycloalkanes or mixtures thereof with a boiling point between 80° C. and 200° C., specifically n-heptane, n-octane or mixtures thereof.

PCT Publication No. WO 2007/047863 discloses a process for recrystallization of laquinimod sodium comprising dissolving laquinimod sodium in water to form an aqueous solution, concentrating the solution to form a concentrated solution, adding a water-miscible anti-solvent to the concentrated solution to form laquinimod sodium crystals, and isolating the laquinimod sodium crystals.

Polymorphism is defined as "the ability of a substance to exist as two or more crystalline phases that have different arrangement and for conformations of the molecule in the crystal lattice. Thus, in the strict sense, polymorphs are different crystalline forms of the same pure substance in which the molecules have different arrangements and/or configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning calorimetry (DSC) and infrared spectrometry (IR).

Solvent medium and mode of isolation play very important role in obtaining one polymorphic form over another.

It has been disclosed in the art that the amorphous forms of a number of pharmaceutical compounds exhibit superior dissolution characteristics and in some cases different bioavailability patterns compared to crystalline forms [Konno T., Chem. Pharm. Bull., 38, 2003 (1990)]. For some therapeutic indications one bioavailability pattern may be favored over another.

The discovery of new polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic.

Hence, there is a need in the art for novel and stable solid state forms of laquinimod and its sodium salt.

SUMMARY

We have now surprisingly and unexpectedly discovered novel polymorphic forms of laquinimod acid and its sodium salt, different from the material obtained according to the teachings of the '851 patent, and having adequate stability and good dissolution properties.

The process for the preparation of laquinimod sodium described in Example 2 of the '851 patent yields a crystalline form, which we denote as Form A2, characterized by an X-ray powder diffraction pattern having peaks expressed as 2-theta angle positions at about 7.22, 8.36, 9.68, 10.00, 11.79, 13.37, 13.78, 14.08, 14.31, 14.62, 15.02, 15.73, 16.14, 16.74, 17.82, 18.20, 18.90, 20.07, 22.09, 23.17, 24.08, 25.10 and 29.35±0.2 degrees substantially as depicted in FIG. 7, and further characterized by an IR spectrum having absorption bands at about 3301, 2971, 2935, 1613, 1585, 1526, 1495, 1414, 1378, 1347, 1328, 1253, 1220, 1178, 1098, 811 and 700±2 cm$^{-1}$ substantially as depicted in FIG. 8, different from the laquinimod sodium crystal forms of the present invention.

In one aspect, provided herein is a novel and stable crystalline form of laquinimod acid, designated as laquinimod crystalline Form A, characterized by an X-ray powder diffraction pattern having peaks expressed as 2-theta angle positions at about 7.15, 12.58, 14.84, 25.09 and 26.38±0.2 degrees.

In another aspect, encompassed herein is a process for preparing the substantially pure and stable crystalline Form A of laquinimod.

It has also been found that the laquinimod crystalline Form A is stable and consistently reproducible and thus useful in the preparation of laquinimod sodium in high purity.

In another aspect, provided herein is a novel and stable crystalline form of laquinimod sodium, designated as laquinimod sodium crystalline Form A1, characterized by an X-ray powder diffraction pattern having peaks expressed as 2-theta angle positions at about 9.1, 10.7 and 11.2±0.2 degrees.

In another aspect, encompassed herein is a process for preparing the substantially pure and stable crystalline Form A1 of laquinimod sodium.

The novel crystalline Form A1 of laquinimod sodium is consistently reproducible, does not have the tendency to convert to other forms and found to be more stable even after being stored at a temperature of about 40° C. at a relative humidity of about 75% for at least about 1 month, specifically for a period of 3 months, or at a temperature of about 25° C. at a relative humidity of about 60% for at least about 6 months. Moreover, the crystalline Form A1 of laquinimod sodium has a tapped density of about 0.4 g/ml to about 0.5 g/ml, is less electrostatic, and has good flow properties which is particularly suitable for bulk preparation and handling. The laquinimod sodium crystalline Form A1 exhibits properties making it suitable for formulating laquinimod sodium.

In another aspect, encompassed herein is a novel process for preparing substantially pure crystalline Form A2 of laquinimod sodium.

In another aspect, provided herein is a novel and stable crystalline form of laquinimod sodium, designated as laquinimod sodium crystalline Form A3, characterized by an X-ray powder diffraction pattern having peaks expressed as 2-theta angle positions at about 6.44, 6.65, 7.72 and 8.77±0.2 degrees.

In another aspect, encompassed herein is a process for preparing the substantially pure and stable crystalline Form A3 of laquinimod sodium.

In another aspect, provided herein is a novel and stable crystalline form of laquinimod sodium, designated as laquinimod sodium crystalline Form A4, characterized by an X-ray powder diffraction pattern having peaks expressed as 2-theta angle positions at about 6.09, 7.46 and 10.42±0.2 degrees.

In another aspect, encompassed herein is a process for preparing the substantially pure and stable crystalline Form A4 of laquinimod sodium.

In another aspect, provided herein is a novel and stable amorphous form of laquinimod sodium and use thereof for the preparation of laquinimod sodium.

In another aspect, encompassed herein is a process for preparing the substantially pure and stable amorphous form of laquinimod sodium.

In another aspect, provided herein is a pharmaceutical composition comprising laquinimod crystalline Form A disclosed herein and one or more pharmaceutically acceptable excipients.

In yet further aspect, encompassed herein is a process for preparing a pharmaceutical formulation comprising combining laquinimod crystalline Form A with one or more pharmaceutically acceptable excipients.

In another aspect, provided herein is a pharmaceutical composition comprising a therapeutically effective amount of any one or a mixture of the amorphous or polymorphic forms of laquinimod sodium disclosed herein, and one or more pharmaceutically acceptable excipients.

In another aspect, provided herein is a pharmaceutical composition comprising any one or a mixture of the amorphous or polymorphic forms of laquinimod sodium prepared according to processes disclosed herein and one or more pharmaceutically acceptable excipients.

In yet another aspect, encompassed herein is a process for preparing a pharmaceutical formulation comprising combining any one or a mixture of the amorphous or polymorphic forms of laquinimod sodium prepared according to processes disclosed herein, with one or more pharmaceutically acceptable excipients.

In another aspect, provided herein is a method for treating a patient suffering from diseases caused by autoimmunity such as multiple sclerosis, insulin-dependent diabetes mellitus, systemic lupus erythematosus, rheumatoid arthritis, inflammatory bowel disease and psoriasis and, furthermore, diseases where pathologic inflammation plays a major role, such as asthma, atherosclerosis, stroke and Alzheimer's disease; comprising administering any one or a mixture of the amorphous or polymorphic forms of laquinimod sodium disclosed herein, or a pharmaceutical composition that comprises any one or a mixture of the amorphous or polymorphic forms of laquinimod sodium disclosed herein along with pharmaceutically acceptable excipients.

In still further aspect, each one or a mixture of the amorphous or polymorphic forms of laquinimod sodium disclosed herein for use in the pharmaceutical compositions has a 90 volume-percent of the particles ($D_{90}$) of less than or equal to about 500 microns, specifically less than or equal to about 300 microns, more specifically less than or equal to about 200 microns, still more specifically less than or equal to about 100 microns, and most specifically less than or equal to about 15 microns.

BRIEF DESCRIPTION OF THE DRAWINGS

FIG. 1 is a characteristic powder X-ray diffraction (XRD) pattern of laquinimod crystalline Form A.

FIG. 2 is a characteristic infra red (IR) spectrum of laquinimod crystalline Form A.

FIG. 3 is a characteristic differential scanning calorimetric (DSC) thermogram of laquinimod crystalline Form A.

FIG. 4 is a characteristic powder X-ray diffraction (XRD) pattern of laquinimod sodium crystalline Form A1.

FIG. 5 is a characteristic infra red (IR) spectrum of laquinimod sodium crystalline Form A1.

FIG. 6 is a characteristic differential scanning calorimetric (DSC) thermogram of laquinimod sodium crystalline Form A1.

FIG. 7 is a characteristic powder X-ray diffraction (XRD) pattern of laquinimod sodium crystalline Form A2.

FIG. 8 is a characteristic infra red (IR) spectrum of laquinimod sodium crystalline Form A2.

FIG. 9 is a characteristic differential scanning calorimetric (DSC) thermogram of laquinimod sodium crystalline Form A2.

FIG. 10 is a characteristic powder X-ray diffraction (XRD) pattern of laquinimod sodium crystalline Form A3.

FIG. 11 is a characteristic infra red (IR) spectrum of laquinimod sodium crystalline Form A3.

FIG. 12 is a characteristic differential scanning calorimetric (DSC) thermogram of laquinimod sodium crystalline Form A3.

FIG. 13 is a characteristic powder X-ray diffraction (XRD) pattern of laquinimod sodium crystalline Form A4.

FIG. 14 is a characteristic infra red (IR) spectrum of laquinimod sodium crystalline Form A4.

FIG. 15 is a characteristic differential scanning calorimetric (DSC) thermogram of laquinimod sodium crystalline Form A4.

FIG. 16 is a characteristic powder X-ray diffraction (XRD) pattern of amorphous laquinimod sodium.

FIG. 17 is a characteristic infra red (IR) spectrum of amorphous laquinimod sodium.

DETAILED DESCRIPTION

According to one aspect, there is provided a novel crystalline form of laquinimod acid, designated as laquinimod crystalline Form A, characterized by at least one, and specifically all, of the following properties:

i) a powder X-ray diffraction pattern substantially in accordance with FIG. 1;
ii) a powder X-ray diffraction pattern having peaks at about 7.15, 12.58, 14.84, 25.09 and 26.38±0.2 degrees 2-theta;
iii) a powder X-ray diffraction pattern having additional peaks at about 6.19, 8.78, 14.04, 14.37, 15.36, 16.20, 18.48, 18.81, 20.44, 20.73, 21.71, 23.21, 23.50, 23.76, 28.96 and 31.08±0.2 degrees 2-theta;
iv) an IR spectrum substantially in accordance with FIG. 2;
v) an IR spectrum having absorption bands at about 3081, 2976, 1647, 1617, 1586, 1562, 1496, 1378, 1327, 1303, 1237, 1197, 812 and 701±2 $cm^{-1}$; and
vi) a DSC thermogram having an endotherm peak at about 240° C. substantially as depicted in FIG. 3.

According to another aspect, there is provided a process for the preparation of a crystalline Form A of laquinimod, comprising:

a) providing a suspension of N-ethyl-N-phenyl-1,2-dihydro-4-hydroxy-5-chloro-1-methyl-2-oxoquinoline-3-carboxamide (laquinimod or laquinimod acid) in a solvent medium comprising an ester solvent and a chlorinated hydrocarbon solvent;
b) optionally, cooling the suspension obtained in step-(a); and
c) recovering crystalline Form A of laquinimod from the suspension.

The process can produce crystalline Form A of laquinimod in substantially pure form.

The term "substantially pure laquinimod crystalline Form A" refers to the laquinimod crystalline Form A having purity greater than about 98%, specifically greater than about 99%, more specifically greater than about 99.3% and still more specifically greater than about 99.5% (measured by HPLC).

The laquinimod crystalline Form A is stable, consistently reproducible, and is particularly suitable for bulk preparation and handling. Moreover, the crystalline Form A of laquinimod is useful intermediate in the preparation of laquinimod sodium in high purity.

The crystalline Form A of laquinimod has good flow properties and stable at room temperature, enhanced temperature, at relative high humidities, and in aqueous media.

In one embodiment, the process disclosed herein provides stable crystalline form of laquinimod. The term "stable crystalline form" refers to stability of the crystalline form under the standard temperature and humidity conditions of testing of pharmaceutical products, wherein the stability is indicated by preservation of the original polymorphic form.

Exemplary halogenated hydrocarbon solvents include, but are not limited to, methylene chloride, 1,2-dichloroethane, chloroform, carbon tetrachloride, and mixtures thereof. A specific halogenated hydrocarbon solvent is methylene chloride. Exemplary ester solvents include, but are not limited to, $C_2$ to $C_6$ alkyl acetates such as methyl acetate, ethyl acetate, n-propyl acetate, isopropyl acetate, n-butyl acetate, isobutyl acetate, tert-butyl acetate, ethyl formate, and mixtures thereof. Specific ester solvents are ethyl acetate, isopropyl acetate, and mixtures thereof.

Step-(a) of providing a suspension of laquinimod includes suspending laquinimod in the solvent medium under stirring at below reflux temperature of the solvent medium used. In one embodiment, the suspension is stirred at a temperature of about 30° C. to about 100° C. for at least 15 minutes and more specifically at about 40° C. to about 80° C. for about 30 minutes to about 5 hours.

As used herein, "reflux temperature" means the temperature at which the solvent or solvent system refluxes or boils at atmospheric pressure.

In another embodiment, the suspension in step-(a) is prepared by reacting 1,2-dichloro-4-hydroxy-5-chloro-1-methyl-2-oxo-quinoline-3-carboxylic acid with N-ethyl aniline in the presence of a suitable coupling agent, optionally in the presence of a base, in a suitable solvent under suitable conditions to produce a reaction mass containing crude laquinimod acid followed by usual work up such as washings, extractions, evaporations etc., and suspending the resulting crude laquinimod in the solvent medium under stirring at below reflux temperature of the solvent medium used, specifically at a temperature of about 30° C. to about 100° C., and more specifically at about 40° C. to about 80° C.

Alternatively, the suspension in step-(a) is prepared by treating a pharmaceutically acceptable salt of laquinimod with an acid to liberate laquinimod acid and suspending the laquinimod acid in the solvent medium.

Pharmaceutically acceptable salts of laquinimod can be obtained from alkali or alkaline earth metals including sodium, calcium, potassium and magnesium, and more specifically sodium.

The treatment of the pharmaceutically acceptable salt of laquinimod with acid is carried out in any solvent and the selection of solvent is not critical. A wide variety of solvents such as chlorinated solvents, hydrocarbon solvents, ether solvents, alcoholic solvents, ketonic solvents, ester solvents etc., can be used.

The acid can be inorganic or organic. Specific acids are hydrochloric acid, hydrobromic acid, sulfuric acid, nitric acid, acetic acid, propionic acid, phosphoric acid, succinic acid, maleic acid, fumaric acid, citric acid, glutaric acid, citraconic acid, glutaconic acid, tartaric acid, malic acid, ascorbic acid, and more specifically hydrochloric acid.

The suspension in step-(b) is specifically cooled at a temperature of below 30° C. under stirring for at least 15 minutes, and more specifically at a temperature of about 10° C. to about 30° C. for about 30 minutes to 2 hours.

The recovering in step-(c) is carried out by methods such as filtration, filtration under vacuum, decantation, centrifugation, or a combination thereof. In one embodiment, the crystalline Form A of laquinimod is recovered by filtration employing a filtration media of, for example, a silica gel or celite.

The substantially pure laquinimod crystalline Form A obtained by above process may be further dried in, for example, a Vacuum Tray Dryer, a Rotocon Vacuum Dryer, a Vacuum Paddle Dryer or a pilot plant Rota vapor, to further lower residual solvents. Drying can be carried out under reduced pressure until the residual solvent content reduces to the desired amount such as an amount that is within the limits given by the International Conference on Harmonization of Technical Requirements for Registration of Pharmaceuticals for Human Use ("ICH") guidelines.

In one embodiment, the drying is carried out at atmospheric pressure or reduced pressures, such as below about 200 mm Hg, or below about 50 mm Hg, at temperatures such as about 35° C. to about 75° C. The drying can be carried out for any desired time period that achieves the desired result, such as about 1 to 20 hours. Drying may also be carried out for shorter or longer periods of time depending on the product specifications. Temperatures and pressures will be chosen based on the volatility of the solvent being used and the foregoing should be considered as only a general guidance. Drying can be suitably carried out in a tray dryer, vacuum oven, air oven, or using a fluidized bed drier, spin flash dryer, flash dryer and the like. Drying equipment selection is well within the ordinary skill in the art.

The purity of the crystalline Form A of laquinimod obtained by the process disclosed herein is greater than about 99%, specifically greater than about 99.5%, more specifically greater than about 99.9%, and most specifically greater than about 99.95% as measured by HPLC. For example, the purity of the laquinimod crystalline Form A can be about 99% to about 99.95%, or about 99.5% to about 99.99%.

According to another aspect, there is provided a novel crystalline form of laquinimod sodium, designated as crystalline Form A1, characterized by at least one, and specifically all, of the following properties:

i) a powder X-ray diffraction pattern substantially in accordance with FIG. 4;

ii) a powder X-ray diffraction pattern having peaks at about 9.1, 10.7 and 11.2±0.2 degrees 2-theta;

iii) a powder X-ray diffraction pattern having additional peaks at about 7.25, 9.72, 10.03, 13.08, 13.91, 14.57, 14.99, 15.69, 16.12, 16.75, 17.57, 18.15, 19.16, 19.87, 20.44, 21.24, 21.68, 21.88, 22.98, 23.79, 24.63 and 25.63±0.2 degrees 2-theta;

iv) an IR spectrum substantially in accordance with FIG. 5;

v) an IR spectrum having absorption bands at about 3377, 3062, 2972, 2933, 1611, 1585, 1528, 1495, 1414, 1377, 1347, 1325, 1255, 1220, 1178, 1098, 811 and 697±2 cm$^{-1}$; and vi) a DSC thermogram substantially in accordance with FIG. 6.

According to another aspect, there is provided a process for the preparation of laquinimod sodium crystalline Form A1, comprising:

a) providing a solution of laquinimod sodium in an alcoholic solvent;

b) optionally, filtering the solvent solution to remove any extraneous matter;

c) optionally, seeding the solution;

d) stirring the solution at about 15-30° C. to form a first reaction mass;

e) cooling the first reaction mass at below about 10° C. to form a second reaction mass; and f) recovering the crystalline Form A1 of laquinimod sodium from the second reaction mass.

The process can produce crystalline Form A1 of laquinimod sodium in substantially pure form.

The term "substantially pure laquinimod sodium crystalline Form A1" refers to the laquinimod sodium crystalline Form A1 having purity greater than about 98%, specifically greater than about 99%, more specifically greater than about 99.5% and still more specifically greater than about 99.9% (measured by HPLC).

In another embodiment, the laquinimod sodium crystalline Form A1 disclosed herein remains in the same crystalline form and stable, when stored at a temperature of about 25±2° C. and at a relative humidity of about 60±5% for a period of at least one month.

In still another embodiment, the laquinimod sodium crystalline Form A1 disclosed herein remains in the same crystalline form and stable, when stored at a temperature of about 25±2° C. and at a relative humidity of about 60±5% for a period of 6 months.

In yet another embodiment, the laquinimod sodium crystalline Form A1 disclosed herein remains in the same crystalline form and stable, when stored at a temperature of about 40±2° C. and at a relative humidity of about 75±5% for a period of at least one month.

In still another embodiment, the laquinimod sodium crystalline Form A1 disclosed herein remains in the same crystalline form and stable, when stored at a temperature of about 40±2° C. and at a relative humidity of about 75±5% for a period of 3 months.

The term "remains stable", as defined herein, refers to lack of formation of impurities, while being stored as described herein. The stability of crystalline Form A1 is measured by maintaining crystalline Form A1 at a temperature of about 40° C. at a relative humidity of about 75% for at least about 1 month, specifically for a period of 3 months, or at a temperature of about 25° C. at a relative humidity of about 60% for a period of 6 months.

In another embodiment, the laquinimod sodium crystalline Form A1 is a free-flowing solid, having a bulk density of at least about 0.30 g/ml, and specifically about 0.30 g/ml to about 0.35 g/ml.

In another embodiment, the laquinimod sodium crystalline Form A1 has a tapped density of at least about 0.40 g/ml, and specifically about 0.45 g/ml to about 0.50 g/ml.

The laquinimod sodium crystalline Form A1 obtained by the process disclosed herein is stable, consistently reproducible and has good flow properties, and is particularly suitable for bulk preparation and handling, and hence, the crystalline Form A1 of laquinimod sodium obtained by the process disclosed herein is suitable for formulating laquinimod sodium.

Exemplary alcohol solvents used in step-(a) include, but are not limited to, $C_1$ to $C_6$ straight or branched chain alcohol solvents such as methanol, ethanol, isopropyl alcohol, butanol, amyl alcohol, hexanol, and mixtures thereof. Specific alcohol solvents are methanol, ethanol, isopropyl alcohol and mixtures thereof, and more specifically ethanol.

Step-(a) of providing a solution of laquinimod sodium includes dissolving laquinimod sodium in the alcoholic solvent, or obtaining an existing solution from a previous processing step.

In one embodiment, the laquinimod sodium is dissolved in the solvent at a temperature of below about reflux temperature of the solvent used, specifically at about 20° C. to about 80° C. and more specifically at about 20° C. to about 60° C.

In another embodiment, the solution in step-(a) is prepared by providing a suspension of laquinimod in a suitable alcoholic solvent followed by combining the suspension with aqueous sodium hydroxide solution to form a clear solution.

The suspension of laquinimod is provided by suspending the laquinimod in the alcoholic solvent under stirring at a temperature of below about reflux temperature of the solvent used, specifically at about 20° C. to about 80° C., and more specifically at about 20° C. to about 40° C. In one embodiment, the suspension of laquinimod is prepared by reacting 1,2-dichloro-4-hydroxy-5-chloro-1-methyl-2-oxo-quinoline-3-carboxylic acid with N-ethyl aniline in the presence of a suitable coupling agent, optionally in the presence of a base, in a suitable solvent under suitable conditions to produce a reaction mass containing crude laquinimod acid followed by usual work up such as washings, extractions, evaporations etc., and suspending the resulting crude laquinimod in the alcoholic solvent under stirring at a temperature of below about reflux temperature of the solvent used, specifically at about 20° C. to about 80° C., and more specifically at about 20° C. to about 40° C.

Combining of the suspension with aqueous sodium hydroxide solution is done in a suitable order, for example, the aqueous sodium hydroxide solution is added to the suspension, or alternatively, the suspension is added to the aqueous sodium hydroxide solution. The addition is, for example, carried out drop wise or in one portion or in more than one portion. The addition is specifically carried out at a temperature of below 50° C. for at least 15 minutes, and more specifically at a temperature of about 15° C. to about 35° C. for about 30 minutes to about 2 hours.

The solution obtained in step-(a) is optionally subjected to carbon treatment or silica get treatment. The carbon treatment or silica get treatment is carried out by methods known in the art, for example, by stirring the solution with finely powdered carbon or silica gel at a temperature of below about 70° C. for at least 15 minutes, specifically at a temperature of about 40° C. to about 70° C. for at least 30 minutes; and filtering the resulting mixture through hyflo to obtain a filtrate containing laquinimod sodium by removing finely powdered carbon or silica gel. Preferably, finely powdered carbon is an active carbon. A specific mesh size of silica gel is 40-500 mesh, and more specifically 60-120 mesh.

The solution in step-(d) is specifically stirred for at least 1 hour, and more specifically for about 2 hours to about 6 hours, at a temperature of about 20° C. to about 30° C.

In one embodiment, the first reaction mass in step-(e) is cooled under stirring at a temperature of about 0-10° C. for at least 15 minutes, and specifically at about 0-5° C. for about 30 minutes to about 4 hours.

The recovering in step-(f) is carried out by methods such as filtration, filtration under vacuum, decantation, centrifugation, or a combination thereof. In one embodiment, the crystalline Form A1 of laquinimod sodium is recovered by filtration employing a filtration media of, for example, a silica gel or celite.

The substantially pure laquinimod sodium crystalline Form A1 obtained by the above process is further dried as described hereinabove.

According to another aspect, there is provided an improved process for preparing laquinimod sodium crystalline Form A2, comprising:
a) providing a solution of laquinimod sodium in an alcoholic solvent;
b) optionally, filtering the solvent solution to remove any extraneous matter;
c) optionally, seeding the solution;
d) stirring the solution at a temperature of about 20-30° C. for at least 1 hour to produce a reaction mass; and
e) recovering the crystalline Form A2 of laquinimod sodium from the reaction mass obtained in step-(d).

In one embodiment, the crystalline Form A2 of laquinimod sodium is characterized by at least one, or more, of the following properties:
i) a powder X-ray diffraction pattern substantially in accordance with FIG. 7;
ii) a powder X-ray diffraction pattern having peaks at about 8.36, 25.10 and 29.35±0.2 degrees 2-theta;
iii) a powder X-ray diffraction pattern having additional peaks at about 7.22, 9.68, 10.00, 11.79, 13.37, 13.78, 14.08, 14.31, 14.62, 15.02, 15.73, 16.14, 16.74, 17.82, 18.20, 18.90, 20.07, 22.09, 23.17 and 24.08±0.2 degrees 2-theta;
iv) an IR spectrum substantially in accordance with FIG. 8;
v) an IR spectrum having absorption bands at about 3301, 2971, 2935, 1613, 1585, 1526, 1495, 1414, 1378, 1347, 1328, 1253, 1220, 1178, 1098, 811 and 700±2 $cm^{-1}$; and
vi) a DSC thermogram substantially in accordance with FIG. 9.

The process can produce crystalline Form A2 of laquinimod sodium in substantially pure form.

The term "substantially pure laquinimod sodium crystalline Form A2" refers to the laquinimod sodium crystalline Form A2 having purity greater than about 98%, specifically greater than about 99%, more specifically greater than about 99.5% and still more specifically greater than about 99.9% (measured by HPLC).

Exemplary alcohol solvents used in step-(a) include, but are not limited to, $C_1$ to $C_6$ straight or branched chain alcohol solvents such as methanol, ethanol, isopropyl alcohol, butanol, amyl alcohol, hexanol, and mixtures thereof. Specific alcohol solvents are methanol, ethanol, isopropyl alcohol and mixtures thereof, and more specifically ethanol, isopropyl alcohol and mixtures thereof.

Step-(a) of providing a solution of laquinimod sodium includes dissolving laquinimod sodium in the alcoholic solvent, or obtaining an existing solution from a previous processing step.

In one embodiment, the laquinimod sodium is dissolved in the solvent at a temperature of below about reflux temperature of the solvent used, specifically at about 20° C. to about 80° C., and more specifically at about 20° C. to about 60° C.

In another embodiment, the solution in step-(a) is prepared by providing a suspension of laquinimod in a suitable alcoholic solvent followed by combining the suspension with aqueous sodium hydroxide solution to form a clear solution as described hereinabove.

In another embodiment, the solution obtained in step-(a) is optionally subjected to carbon treatment or silica get treatment as described above.

The solution in step-(d) is specifically stirred for at least 5 hours, more specifically for about 6 hours to about 30 hours, and most specifically for about 15 hours to about 25 hours, at a temperature of about 25° C. to about 30° C.

The recovering in step-(e) is carried out by methods such as filtration, filtration under vacuum, decantation, centrifugation, or a combination thereof. In one embodiment, the crystalline Form A2 of laquinimod sodium is recovered by filtration employing a filtration media of, for example, a silica gel or celite.

The substantially pure laquinimod sodium crystalline Form A2 obtained by the above process is further dried as described hereinabove.

According to another aspect, there is provided a novel crystalline form of laquinimod sodium, designated as crystalline Form A3, characterized by at least one, and specifically all, of the following properties:
i) a powder X-ray diffraction pattern substantially in accordance with FIG. 10;
ii) a powder X-ray diffraction pattern having peaks at about 6.44, 6.65, 7.72 and 8.77±0.2 degrees 2-theta;
iii) a powder X-ray diffraction pattern having additional peaks at about 9.31, 9.60, 10.71, 11.14, 11.66, 13.25, 14.61, 15.32, 17.62, 17.98, 18.54, 19.21, 21.38, 22.11, 22.59, 23.43, 23.99, 25.04, 25.44 and 27.86±0.2 degrees 2-theta;
iv) an IR spectrum substantially in accordance with FIG. 11;
v) an IR spectrum having absorption bands at about 3368, 2970, 2936, 1615, 1583, 1526, 1495, 1412, 1377, 1344, 1326, 1253, 1218, 1177, 1097, 813 and 699±2 $cm^{-1}$; and
vi) a DSC thermogram substantially in accordance with FIG. 12.

According to another aspect, there is provided a process for the preparation of laquinimod sodium crystalline Form A3, comprising:
a) providing a solution of laquinimod sodium in an alcoholic solvent;
b) optionally, filtering the solvent solution to remove any extraneous matter;
c) optionally, seeding the solution;
d) admixing the solution with an anti-solvent; and
e) recovering the crystalline Form A3 of laquinimod sodium from the reaction mass obtained in step-(d).

The process can produce crystalline Form A3 of laquinimod sodium in substantially pure form.

The term "substantially pure laquinimod sodium crystalline Form A3" refers to the laquinimod sodium crystalline Form A3 having purity greater than about 98%, specifically greater than about 99%, more specifically greater than about 99.5% and still more specifically greater than about 99.9% (measured by HPLC).

The laquinimod sodium crystalline Form A3 is stable, consistently reproducible and has good flow properties, and is particularly suitable for bulk preparation and handling, and hence, the laquinimod sodium crystalline Form A3 disclosed herein is suitable for formulating laquinimod sodium.

Exemplary alcohol solvents used in step-(a) include, but are not limited to, $C_1$ to $C_6$ straight or branched chain alcohol solvents such as methanol, ethanol, isopropyl alcohol, butanol, amyl alcohol, hexanol, and mixtures thereof. Specific alcohol solvents are methanol, ethanol, isopropyl alcohol and mixtures thereof, and more specifically ethanol.

Step-(a) of providing a solution of laquinimod sodium includes dissolving laquinimod sodium in the alcoholic solvent, or obtaining an existing solution from a previous processing step.

In one embodiment, the laquinimod sodium is dissolved in the solvent at a temperature of below about reflux temperature of the solvent used, specifically at about 20° C. to about 80° C., and more specifically at about 20° C. to about 60° C.

In another embodiment, the solution in step-(a) is prepared by providing a suspension of laquinimod in a suitable alcoholic solvent followed by combining the suspension with aqueous sodium hydroxide solution to form a clear solution as described hereinabove.

In another embodiment, the solution obtained in step-(a) is optionally subjected to carbon treatment or silica get treatment as described above.

Exemplary anti-solvents used in step-(d) include, but are not limited to, an ether, a hydrocarbon, and mixtures thereof. Exemplary ether solvents include, but are not limited to, diisopropyl ether, diethyl ether, tetrahydrofuran, dioxane, and the like, and mixtures thereof. Exemplary hydrocarbon solvents include, but are not limited to, n-pentane, n-hexane and n-heptane and their isomers, cyclohexane, toluene, xylene, and mixtures thereof. Specific anti-solvents are diisopropyl ether, diethyl ether and mixtures thereof.

The term "Anti-solvent" refers to a solvent which when added to an existing solution of a substance reduces the solubility of the substance.

The admixing in step-(d) is done in a suitable order, for example, the solution is added to the anti-solvent, or alternatively, the anti-solvent is added to the solution. The addition is, for example, carried out drop wise or in one portion or in more than one portion. The addition is specifically carried out at a temperature of below 50° C. for at least 15 minutes and more specifically at a temperature of about 15° C. to about 35° C. for about 20 minutes to about 2 hours. After completion of addition process, the resulting mass is stirred for at least 2 hours, more specifically for about 6 hours to about 30 hours, and most specifically for about 15 hours to about 25 hours, at a temperature of about 20° C. to about 30° C.

The recovering in step-(e) is carried out by methods such as filtration, filtration under vacuum, decantation, centrifugation, or a combination thereof. In one embodiment, the crystalline Form A3 of laquinimod sodium is recovered by filtration employing a filtration media of, for example, a silica gel or celite.

The substantially pure laquinimod sodium crystalline Form A3 obtained by the above process is further dried as described hereinabove.

According to another aspect, there is provided a novel crystalline form of laquinimod sodium, designated as crystalline Form A4, characterized by at least one, and specifically all, of the following properties:
i) a powder X-ray diffraction pattern substantially in accordance with FIG. 13;

ii) a powder X-ray diffraction pattern having peaks at about 6.09, 7.46 and 10.42±0.2 degrees 2-theta;
iii) a powder X-ray diffraction pattern having additional peaks at about 7.82, 8.47, 10.12, 14.15, 16.10, 18.95, 22.66, 23.50, 25.84, 26.13, 28.24, 29.07, 29.81, 31.62 and 33.94±0.2 degrees 2-theta;
iv) an IR spectrum substantially in accordance with FIG. 14;
v) an IR spectrum having absorption bands at about 3413, 2974, 2935, 1612, 1584, 1524, 1495, 1413, 1377, 1346, 1327, 1253, 1219, 1177, 1097, 811 and 698±2 cm$^{-1}$; and
vi) a DSC thermogram substantially in accordance with FIG. 15.

According to another aspect, there is provided a process for the preparation of laquinimod sodium crystalline Form A4, comprising:
a) providing a solution of laquinimod sodium in a ketone solvent;
b) optionally, filtering the solvent solution to remove any extraneous matter;
c) optionally, seeding the solution; and
d) isolating crystalline Form A4 of laquinimod sodium from the solution.

The process can produce crystalline Form A4 of laquinimod sodium in substantially pure form.

The term "substantially pure laquinimod sodium crystalline Form A4" refers to the laquinimod sodium crystalline Form A4 having purity greater than about 98%, specifically greater than about 99%, more specifically greater than about 99.5% and still more specifically greater than about 99.9% (measured by HPLC).

The laquinimod sodium crystalline Form A4 is stable, consistently reproducible and has good flow properties, and is particularly suitable for bulk preparation and handling, and hence, the laquinimod sodium crystalline Form A4 disclosed herein is suitable for formulating laquinimod sodium.

Exemplary ketone solvents used in step-(a) include, but are not limited to, acetone, methyl ethyl ketone, methyl isobutyl ketone, methyl tert-butyl ketone and the like, and mixtures thereof. A specific ketone solvent is acetone.

Step-(a) of providing a solution of laquinimod sodium includes dissolving laquinimod sodium in the ketone solvent, or obtaining an existing solution from a previous processing step.

In one embodiment, the laquinimod sodium is dissolved in the ketone solvent at a temperature of below about reflux temperature of the solvent used, specifically at about 40° C. to about 80° C., and most specifically at about 50° C. to about 70° C.

In another embodiment, the solution in step-(a) is prepared by providing a suspension of laquinimod in a suitable ketone solvent followed by combining the suspension with sodium hydroxide base and then heating the resulting mass to form a clear solution.

In one embodiment, the suspension of laquinimod is provided by the methods as described hereinabove.

In another embodiment, the solution obtained in step-(a) is optionally subjected to carbon treatment or silica get treatment as described above.

The isolation of pure laquinimod sodium crystalline Form A4 in step-(d) is carried out by crystallization methods such as cooling, seeding, partial removal of the solvent from the solution, by adding an anti-solvent to the solution, or a combination thereof.

In one embodiment, the crystallization is carried out by cooling the solution at a temperature of below 30° C., and more specifically at about 0° C. to about 25° C.

The solid obtained in step-(d) is recovered by methods such as filtration, filtration under vacuum, decantation, centrifugation, or a combination thereof. In one embodiment, the crystalline Form A4 of laquinimod sodium is recovered by filtration employing a filtration media of, for example, a silica gel or celite.

The substantially pure laquinimod sodium crystalline Form A4 obtained by the above process is further dried as described hereinabove.

According to another aspect, there is provided a stable and substantially pure amorphous form of laquinimod sodium.

Amorphous form of laquinimod sodium is characterized by at least one, and specifically all, of the following properties: a powder XRD pattern substantially in accordance with FIG. 16; an IR spectrum substantially in accordance with FIG. 17; and an IR spectrum having absorption bands at about 3401, 2973, 2936, 1612, 1584, 1525, 1494, 1412, 1377, 1345, 1327, 1253, 1219, 1177, 1097, 813 and 698±2 cm$^{-1}$. The X-ray powder diffraction pattern shows no peaks, thus demonstrating the amorphous nature of the product.

According to another aspect, there is provided a process for the preparation of an amorphous form of laquinimod sodium, comprising:
a) providing a solution of laquinimod sodium in a solvent selected from the group consisting of an alcohol, a ketone, and mixtures thereof;
b) optionally, filtering the solvent solution to remove any extraneous matter;
c) optionally, seeding the solution; and
d) substantially removing the solvent from the solution to provide amorphous form of laquinimod sodium.

The term "substantially removing" the solvent refers to at least 80%, specifically greater than about 85%, more specifically greater than about 90%, still more specifically greater than about 99%, and most specifically essentially complete (100%), removal of the solvent from the solvent solution.

The process can produce amorphous form of laquinimod sodium in substantially pure form.

The term "substantially pure amorphous laquinimod sodium" refers to the amorphous laquinimod sodium having purity greater than about 98%, specifically greater than about 99%, more specifically greater than about 99.5% and still more specifically greater than about 99.9% (measured by HPLC).

The amorphous laquinimod sodium obtained by the process disclosed herein is stable, consistently reproducible and has good flow properties, and is particularly suitable for bulk preparation and handling, and hence, the amorphous laquinimod sodium is suitable for formulating laquinimod sodium.

Exemplary alcohol solvents used in step-(a) include, but are not limited to, $C_1$ to $C_6$ straight or branched chain alcohol solvents such as methanol, ethanol, isopropyl alcohol, butanol, amyl alcohol, hexanol, and mixtures thereof. Specific alcohol solvents are methanol, ethanol, isopropyl alcohol and mixtures thereof, and more specifically methanol. Exemplary ketone solvents used in step-(a) include, but are not limited to, acetone, methyl ethyl ketone, methyl isobutyl ketone, methyl tert-butyl ketone and the like, and mixtures thereof. A specific ketone solvent is acetone.

Step-(a) of providing a solution of laquinimod sodium includes dissolving laquinimod sodium in the solvent, or obtaining an existing solution from a previous processing step.

In one embodiment, the laquinimod sodium is dissolved in the solvent at a temperature of below about reflux temperature of the solvent used, specifically at about 20° C. to about 80° C., and most specifically at about 20° C. to about 70° C.

In another embodiment, the solution in step-(a) is prepared by providing a suspension of laquinimod in a solvent selected from the group consisting of an alcohol, a ketone, and mixtures thereof; combining the suspension with aqueous sodium hydroxide solution and optionally heating the resulting mass until to form a clear solution.

In one embodiment, the suspension of laquinimod is provided by the methods as described hereinabove.

In another embodiment, the solution obtained in step-(a) is optionally subjected to carbon treatment or silica get treatment as described above.

Removal of solvent in step-(d) is accomplished, for example, by substantially complete evaporation of the solvent, concentrating the solution or distillation of solvent, under inert atmosphere to obtain amorphous laquinimod sodium.

In one embodiment, the solvent is removed by evaporation. Evaporation can be achieved at sub-zero temperatures by lyophilisation or freeze-drying techniques. The solution may also be completely evaporated in, for example, a pilot plant Rota vapor, a Vacuum Paddle Dryer or in a conventional reactor under vacuum above about 720 mm Hg by flash evaporation techniques by using an agitated thin film dryer ("ATFD"), or evaporated by spray drying to obtain a dry amorphous powder.

The distillation process can be performed at atmospheric pressure or reduced pressure. Specifically, the solvent is removed at a pressure of about 760 mm Hg or less, more specifically at about 400 mm Hg or less, still more specifically at about 80 mm Hg or less, and most specifically from about 30 to about 80 mm Hg.

Solvents can also be removed by spray-drying, in which a solution of laquinimod sodium is sprayed into the spray drier at the flow rate ranging from 10 to 300 ml/hr, specifically 40 to 200 ml/hr. The air inlet temperature to the spray drier used may range from about 30° C. to about 150° C., specifically from about 65° C. to about 110° C. and the outlet air temperature used may range from about 30° C. to about 90° C.

Another suitable method is vertical agitated thin-film drying (or evaporation). Agitated thin film evaporation technology involves separating the volatile component using indirect heat transfer coupled with mechanical agitation of the flowing film under controlled conditions. In vertical agitated thin-film drying (or evaporation) (ATFD-V), the starting solution is fed from the top into a cylindrical space between a centered rotary agitator and an outside heating jacket. The rotor rotation agitates the downside-flowing solution while the heating jacket heats it.

The substantially pure amorphous form of laquinimod sodium obtained by the above process is further dried as described hereinabove.

Further encompassed herein is the use of the polymorphic forms of laquinimod and its sodium salt disclosed herein for the manufacture of a pharmaceutical composition together with a pharmaceutically acceptable carrier.

A specific pharmaceutical composition of the polymorphic forms of laquinimod and its sodium salt is selected from a solid dosage form and an oral suspension.

In one embodiment, each one or a mixture of the solid state forms of laquinimod sodium (Form A1, Form A3, Form A4 and amorphous form) disclosed herein has a $D_{90}$ particle size of less than or equal to about 500 microns, specifically less than or equal to about 300 microns, more specifically less than or equal to about 200 microns, still more specifically less than or equal to about 100 microns, and most specifically less than or equal to about 15 microns.

In another embodiment, each one or a mixture of the amorphous or polymorphic forms of laquinimod sodium disclosed herein for use in the pharmaceutical compositions has a 90 volume-percent of the particles ($D_{90}$) of less than or equal to about 500 microns, specifically less than or equal to about 300 microns, more specifically less than or equal to about 200 microns, still more specifically less than or equal to about 100 microns, and most specifically less than or equal to about 15 microns.

In another embodiment, the particle sizes of the amorphous or polymorphic forms of laquinimod sodium can be achieved by a mechanical process of reducing the size of particles which includes any one or more of cutting, chipping, crushing, milling, grinding, micronizing, trituration or other particle size reduction methods known in the art, to bring the solid state form to the desired particle size range.

According to another aspect, there is provided a method for treating a patient suffering from diseases caused by autoimmunity such as multiple sclerosis, insulin-dependent diabetes mellitus, systemic lupus erythematosus, rheumatoid arthritis, inflammatory bowel disease and psoriasis and, furthermore, diseases where pathologic inflammation plays a major role, such as asthma, atherosclerosis, stroke and Alzheimer's disease; comprising administering any one or a mixture of the amorphous or polymorphic forms of laquinimod sodium disclosed herein, or a pharmaceutical composition that comprises any one or a mixture of the amorphous or polymorphic forms of laquinimod sodium disclosed herein along with pharmaceutically acceptable excipients.

According to another aspect, there is provided pharmaceutical compositions comprising laquinimod crystalline Form A, and one or more pharmaceutically acceptable excipients.

According to another aspect, there is provided pharmaceutical compositions comprising laquinimod crystalline Form A prepared according to process disclosed herein and one or more pharmaceutically acceptable excipients.

According to another aspect, there is provided a process for preparing a pharmaceutical formulation comprising combining laquinimod crystalline Form A with one or more pharmaceutically acceptable excipients.

According to another aspect, there is provided pharmaceutical compositions comprising a therapeutically effective amount of any one or a mixture of the amorphous or polymorphic forms of laquinimod sodium disclosed herein, and one or more pharmaceutically acceptable excipients.

According to another aspect, there is provided pharmaceutical compositions comprising any one or a mixture of the amorphous or polymorphic forms of laquinimod sodium prepared according to processes disclosed herein and one or more pharmaceutically acceptable excipients.

According to another aspect of the present invention, there is provided a process for preparing a pharmaceutical formulation comprising combining any one or a mixture of the amorphous or polymorphic forms of laquinimod sodium prepared according to processes disclosed herein, with one or more pharmaceutically acceptable excipients.

Yet in another embodiment, pharmaceutical compositions comprise at least a therapeutically effective amount of any one or a mixture of the amorphous or polymorphic forms of laquinimod sodium disclosed herein. Such pharmaceutical compositions may be administered to a mammalian patient in a dosage form, e.g., solid, liquid, powder, elixir, aerosol, syrups, injectable solution, etc. Dosage forms may be adapted for administration to the patient by oral, buccal, parenteral, ophthalmic, rectal and transdermal routes or any other acceptable route of administration. Oral dosage forms include, but are not limited to, tablets, pills, capsules, syrup, troches, sachets, suspensions, powders, lozenges, elixirs and the like. The amorphous or polymorphic forms of laquinimod sodium may also be administered as suppositories, ophthalmic ointments and suspensions, and parenteral suspensions, which are administered by other routes.

The pharmaceutical compositions further contain one or more pharmaceutically acceptable excipients. Suitable excipients and the amounts to use may be readily determined by the formulation scientist based upon experience and consideration of standard procedures and reference works in the field, e.g., the buffering agents, sweetening agents, binders, diluents, fillers, lubricants, wetting agents and disintegrants described hereinabove.

In another embodiment, there is provided a pharmaceutical composition comprising laquinimod sodium crystalline Form A1 and one or more pharmaceutically acceptable excipients.

In another embodiment, there is provided a pharmaceutical composition comprising laquinimod sodium crystalline Form A3 and one or more pharmaceutically acceptable excipients.

In another embodiment, there is provided a pharmaceutical composition comprising laquinimod sodium crystalline Form A4 and one or more pharmaceutically acceptable excipients.

In another embodiment, there is provided a pharmaceutical composition comprising the amorphous form of laquinimod sodium and one or more pharmaceutically acceptable excipients.

In one embodiment, capsule dosage forms contain the amorphous or polymorphic forms of laquinimod sodium within a capsule which may be coated with gelatin. Tablets and powders may also be coated with an enteric coating. Suitable enteric coating include phthalic acid cellulose acetate, hydroxypropylmethyl cellulose phthalate, polyvinyl alcohol phthalate, carboxy methyl ethyl cellulose, a copolymer of styrene and maleic acid, a copolymer of methacrylic acid and methyl methacrylate, and like materials, and if desired, the coating agents may be employed with suitable plasticizers and/or extending agents. A coated capsule or tablet may have a coating on the surface thereof or may be a capsule or tablet comprising a powder or granules with an enteric-coating.

Tableting compositions may have few or many components depending upon the tableting method used, the release rate desired and other factors. For example, the compositions described herein may contain diluents such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents such calcium carbonate and calcium diphosphate and other diluents known to one of ordinary skill in the art. Yet other suitable diluents include waxes, sugars (e.g. lactose) and sugar alcohols such as mannitol and sorbitol, acrylate polymers and copolymers, as well as pectin, dextrin and gelatin.

Other excipients include binders, such as acacia gum, pregelatinized starch, sodium alginate, glucose and other binders used in wet and dry granulation and direct compression tableting processes; disintegrants such as sodium starch glycolate, crospovidone, low-substituted hydroxypropyl cellulose and others; lubricants like magnesium and calcium stearate and sodium stearyl fumarate; flavorings; sweeteners; preservatives; pharmaceutically acceptable dyes and glidants such as silicon dioxide.

Instrumental Details:
High Performance Liquid Chromatography (HPLC):
The purity was measured by high performance liquid chromatography under the following conditions:
Apparatus: Water's HPLC system having alliance 2695 model pump and 2487 (UV) detector with Empower chromatography software or its equivalent.
Chromatographic Parameters:
Column: Hypersil (C-18 column)
Detector: UV at 220 nm
Flow rate: 1.0 ml/min
Injection volume: 10.0 µL
Run time: 50 min
Column temperature: 30° C.
Sample temperature: Ambient
Diluent: Water:Acetonitrile—50:50 (% v/v)
Solution A: 2.0 ml TEA dissolved in 1000 ml water and pH=2.2 adjusted with $H_3PO_4$
Solution B: Acetonitrile: Methanol—50:50 (v/v)
X-Ray Powder Diffraction (P-XRD):
The X-Ray powder diffraction was measured by an X-ray powder diffractometer equipped with a Cu-anode ($\lambda$=1.54 Angstrom), X-ray source operated at 40 kV, 40 mA and a Ni filter is used to strip K-beta radiation. Two-theta calibration is performed using an NIST SRM 1976, Corundum standard. The sample was analyzed using the following instrument parameters: measuring range=3-45° 2θ; step width=0.01579°; and measuring time per step=0.11 second.
Infra-Red Spectroscopy (FT-IR):
FT-IR spectroscopy was carried out with a Perkin Elmer Spectrum 100 series spectrometer. For the production of the KBr compacts approximately 2 mg of sample was powdered with 200 mg of KBr. The spectra were recorded in transmission mode ranging from 3800 to 450 $cm^{-1}$.
Differential Scanning Calorimetry (DSC):
DSC (Differential Scanning calorimetry) measurements were performed with a Differential Scanning calorimeter (Perkin Elmer diamond DSC) at a scan rate of 10° C. per minute.
Bulk Density Method of Analysis
About 10 g of sample was placed in a 25 mL measuring cylinder and measured the volume using the following formula:

Bulk density=Weight of the sample (g)/Volume of the sample (mL)

Tap Density Method of Analysis
About 10 g of sample was placed in a 25 mL measuring cylinder and measured the initial volume. The measuring cylinder was kept in a Sotax Tapping instrument (USP II) and measured the volume of the sample every 50 tappings until a constant volume is obtained using the following formula:

Tap Density=Weight of the sample (g)/constant Volume of the sample after tapping (mL)

The following examples are given for the purpose of illustrating the present disclosure and should not be considered as limitation on the scope or spirit of the disclosure.

EXAMPLES

Example 1

Preparation of crystalline Form A of N-ethyl-N-phenyl-1,2-dihydro-4-hydroxy-5-chloro-1-methyl-2-oxoquinoline-3-carboxamide (Laquinimod or Laquinimod acid)

N-Ethyl aniline (21.22 gm) was dissolved in methylene chloride (925 ml) at 25-30° C. under nitrogen atmosphere.

Dichlorotriphenyl phosphorane (97.25 gm) was added to the solution followed by 1,2-Dichloro-4-hydroxy-5-chloro-1-methyl-2-oxo-quinoline-3-carboxylic acid (37 gm) at 25-30° C. The reaction mixture was heated to reflux temperature (40-45° C.) and then stirred for 6 hours at reflux. The resulting mass was cooled to 25-30° C. followed by the addition of water (370 ml) and then stirred for 15 minutes. The resulting two layers were separated, the organic layer was washed with water (370 ml) at 25-30° C. and then distilled out the methylene chloride under vacuum at 40-45° C. This was followed by the addition of methylene chloride (37 ml) and ethyl acetate (370 ml) at 40-45° C., the resulting suspension was heated to 60-65° C. and then stirred for 15 minutes at the same temperature. The resulting mass was cooled to 25-30° C. followed by stirring for 1 hour. The resulting solid was filtered, washed with ethyl acetate (2×74 ml) at 25-30° C. and then dried the solid at 50-55° C. in an air oven for 16 hours to produce 40 gm of crystalline Form A of Laquinimod. (HPLC Purity: 99.32%).

Example 2

Preparation of crystalline Form A1 of N-ethyl-N-phenyl-1,2-dihydro-4-hydroxy-5-chloro-1-methyl-2-oxoquinoline-3-carboxamide sodium (Laquinimod sodium)

N-Ethyl-N-phenyl-1,2-dihydro-4-hydroxy-5-chloro-1-methyl-2-oxoquinoline-3-carboxamide (35 gm) was suspended in ethanol (140 ml) at 20-25° C. under stirring followed by the addition of freshly prepared sodium hydroxide solution (4.13 gm of sodium hydroxide in 11 ml of water) at 20-25° C. and then stirred for 15-30 minutes at 25-30° C. The resulting solution was filtered through a hyflow super cell bed and the bed was washed with ethanol (105 ml) at 25-30° C. The resulting filtrate was seeded with pure laquinimod sodium (0.175 gm) and then stirred for 4 hours at 25-30° C. The resulting mass was cooled to 0-5° C. followed by stirring for 2 hours at the same temperature. The resulting white colored solid was filtered, washed with chilled ethanol (38 ml) and then dried under vacuum at 60-65° C. to yield 28 gm of laquinimod sodium in crystalline Form A1 (HPLC Purity: 99.9%; Bulk density: 0.333 g/ml; Tapped density: 0.476 g/ml; and Particle size distribution: d(0.9)=26.3 microns).

Example 3

Preparation of crystalline Form A2 of N-ethyl-N-phenyl-1,2-dihydro-4-hydroxy-5-chloro-1-methyl-2-oxoquinoline-3-carboxamide sodium (Laquinimod sodium)

N-Ethyl-N-phenyl-1,2-dihydro-4-hydroxy-5-chloro-1-methyl-2-oxoquinoline-3-carboxamide (18 gm) and ethanol (180 ml) were stirred at 25-30° C. for 15 minutes followed by the addition of 40% sodium hydroxide solution (5.6 ml) at 25-30° C. in 10 minutes. The resulted clear solution was stirred at 25-30° C. for 20 hours. The precipitated white colored solid was filtered, washed with ethanol (20 ml) and then dried at 55-60° C. to a constant weight to yield 13 gm of laquinimod sodium in crystalline Form A2.

Example 4

Preparation of crystalline Form A2 of N-ethyl-N-phenyl-1,2-dihydro-4-hydroxy-5-chloro-1-methyl-2-oxoquinoline-3-carboxamide sodium (Laquinimod sodium)

N-Ethyl-N-phenyl-1,2-dihydro-4-hydroxy-5-chloro-1-methyl-2-oxoquinoline-3-carboxamide (15 gm) was suspended in isopropyl alcohol (100 ml) at 25-30° C. under stirring followed by the addition of freshly prepared sodium hydroxide solution (1.4 gm of sodium hydroxide in 3.5 ml of water) at 20-25° C. and then stirred for 15-30 minutes at 25-30° C. The resulting solution was filtered through a hyflow supercell bed and the bed was washed with isopropyl alcohol (50 ml) at 25-30° C. The resulting filtrate was stirred for 20 hours at 25-30° C. The resulting white colored solid was filtered, washed with chilled isopropyl alcohol (20 ml) and then dried in air oven at 60-65° C. to yield 9 gm of laquinimod sodium in crystalline Form A2 (HPLC Purity: 99.8%).

Example 5

Preparation of crystalline Form A3 of N-ethyl-N-phenyl-1,2-dihydro-4-hydroxy-5-chloro-1-methyl-2-oxoquinoline-3-carboxamide sodium (Laquinimod sodium)

Laquinimod sodium (1.5 gm) was dissolved in methanol (10 ml) at 25-30° C. and stirred for 30 minutes. The resulting clear solution was filtered through a hyflow bed and the filtrate was added slowly to diisopropyl ether (500 ml) in 15 minutes at 25-30° C. The resulting mass was stirred for 24 hours at 25-30° C. The separated white colored solid was filtered, washed with diisopropyl ether (20 ml) and then dried at 55-60° C. to produce 1.3 gm of laquinimod sodium in crystalline Form A3.

Example 6

Preparation of crystalline Form A4 of N-ethyl-N-phenyl-1,2-dihydro-4-hydroxy-5-chloro-1-methyl-2-oxoquinoline-3-carboxamide sodium (Laquinimod sodium)

Laquinimod sodium (2 gm) was dissolved in acetone (10 ml) at 55-60° C. and then stirred for 30 minutes. The resulted clear solution was cooled to 25-30° C. in 30 minutes and the resulting mass was then stirred for 1 hour at 25-30° C. The separated solid was filtered and then dried at 53° C. to a constant weight to produce 1.1 gm laquinimod sodium in crystalline Form A4.

Example 7

Preparation of Amorphous Form of Laquinimod Sodium

Laquinimod sodium (1.5 gm) was dissolved in methanol (10 ml) and stirred for 30 minutes at 25-30° C. The resulted clear solution was filtered through hyflow bed. Methanol was distilled off under vacuum using rotary evaporator at 50-55° C. to afford 1.2 gm of amorphous laquinimod sodium.

Example 8

Stability of Laquinimod sodium Crystalline Form A1

Laquinimod sodium crystalline Form A1 was prepared according to the process exemplified in Example 2 and was packed in a self-sealing low-density polyethylene (LDPE) bag. The material was stored for 6 months at a relative humidity of about 60±5% at room temperature (at 25±2° C.) and checked for polymorphic stability.

The material was found to retain its polymorphic form after six months of holding, as indicated by maintenance of the original P-XRD pattern.

Example 9

Stability of Laquinimod Sodium Crystalline Form A1

Laquinimod sodium crystalline Form A1 was prepared according to the process exemplified in Example 2 and was packed in a self-sealing low-density polyethylene (LDPE) bag. The material was stored for 3 months at a relative humidity of about 75±5% at a temperature of about 40±2° C. and checked for polymorphic stability.

The material was found to retain its polymorphic form after three months of holding, as indicated by maintenance of the original P-XRD pattern.

Unless otherwise indicated, the following definitions are set forth to illustrate and define the meaning and scope of the various terms used to describe the invention herein.

The term "crystalline polymorph" refers to a crystal modification that can be characterized by analytical methods such as X-ray powder diffraction, IR-spectroscopy, differential scanning calorimetry (DSC) or by its melting point.

The term "stable crystalline form" refers to stability of the crystalline form under the standard temperature and humidity conditions of testing of pharmaceutical products, wherein the stability is indicated by preservation of the original polymorphic form.

The term "amorphous" means a solid without long-range crystalline order. Amorphous form of laquinimod sodium specifically contains less than about 10% crystalline forms of laquinimod sodium, more specifically less than 5% crystalline forms of laquinimod sodium, and still more specifically is essentially free of crystalline forms of laquinimod sodium. "Essentially free of crystalline forms of laquinimod sodium" means that no crystalline polymorph forms of laquinimod sodium can be detected within the limits of a powder X-ray diffractometer.

The term "pharmaceutically acceptable" means that which is useful in preparing a pharmaceutical composition that is generally non-toxic and is not biologically undesirable and includes that which is acceptable for veterinary use and/or human pharmaceutical use.

The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions encompass any composition made by admixing the active ingredient, active ingredient dispersion or composite, additional active ingredient(s), and pharmaceutically acceptable excipients.

The term "therapeutically effective amount" as used herein means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

The term "delivering" as used herein means providing a therapeutically effective amount of an active ingredient to a particular location within a host causing a therapeutically effective blood concentration of the active ingredient at the particular location. This can be accomplished, e.g., by topical, local or by systemic administration of the active ingredient to the host.

The term "buffering agent" as used herein is intended to mean a compound used to resist a change in pH upon dilution or addition of acid of alkali. Such compounds include, by way of example and without limitation, potassium metaphosphate, potassium phosphate, monobasic sodium acetate and sodium citrate anhydrous and dehydrate and other such material known to those of ordinary skill in the art.

The term "sweetening agent" as used herein is intended to mean a compound used to impart sweetness to a formulation. Such compounds include, by way of example and without limitation, aspartame, dextrose, glycerin, mannitol, saccharin sodium, sorbitol, sucrose, fructose and other such materials known to those of ordinary skill in the art.

The term "binders" as used herein is intended to mean substances used to cause adhesion of powder particles in granulations. Such compounds include, by way of example and without limitation, acacia, alginic acid, tragacanth, carboxymethylcellulose sodium, polyvinylpyrrolidone, compressible sugar (e.g., NuTab), ethylcellulose, gelatin, liquid glucose, methylcellulose, pregelatinized starch, starch, polyethylene glycol, guar gum, polysaccharide, bentonites, sugars, invert sugars, poloxamers (PLURONIC™ F68, PLURONIC™ F127), collagen, albumin, celluloses in non-aqueous solvents, polypropylene glycol, polyoxyethylene-polypropylene copolymer, polyethylene ester, polyethylene sorbitan ester, polyethylene oxide, microcrystalline cellulose, combinations thereof and other material known to those of ordinary skill in the art.

The term "diluent" or "filler" as used herein is intended to mean inert substances used as fillers to create the desired bulk, flow properties, and compression characteristics in the preparation of solid dosage formulations. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

The term "glidant" as used herein is intended to mean agents used in solid dosage formulations to improve flow-properties during tablet compression and to produce an anti-caking effect. Such compounds include, by way of example and without limitation, colloidal silica, calcium silicate, magnesium silicate, silicon hydrogel, cornstarch, talc, combinations thereof and other such materials known to those of ordinary skill in the art.

The term "lubricant" as used herein is intended to mean substances used in solid dosage formulations to reduce friction during compression of the solid dosage. Such compounds include, by way of example and without limitation, calcium stearate, magnesium stearate, mineral oil, stearic acid, zinc stearate, combinations thereof and other such materials known to those of ordinary skill in the art.

The term "disintegrant" as used herein is intended to mean a compound used in solid dosage formulations to promote the disruption of the solid mass into smaller particles which are more readily dispersed or dissolved. Exemplary disintegrants include, by way of example and without limitation, starches such as corn starch, potato starch, pregelatinized, sweeteners, clays, such as bentonite, microcrystalline cellulose (e.g., Avicel™), carsium (e.g., Amberlite™), alginates, sodium starch glycolate, gums such as agar, guar, locust bean, karaya, pectin, tragacanth, combinations thereof and other such materials known to those of ordinary skill in the art.

The term "wetting agent" as used herein is intended to mean a compound used to aid in attaining intimate contact between solid particles and liquids. Exemplary wetting agents include, by way of example and without limitation, gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters, (e.g., TWEEN™s), polyethylene glycols, polyoxyethylene stearates colloidal silicon dioxide, phosphates, sodium dodecylsulfate, carboxymethylcellulose calcium, carboxymethylcellulose sodium, methylcellulose, hydroxyethyl cellulose, hydroxylpropylcellulose, hydroxypropylmethylcellulose phthalate, noncrystalline cellulose, magnesium aluminum silicate, triethanolamine, polyvinyl alcohol, and polyvinylpyrrolidone (PVP). Tyloxapol (a nonionic liquid polymer of the alkyl aryl polyether alcohol type) is another useful wetting agent, combinations thereof and other such materials known to those of ordinary skill in the art.

The term "micronization" used herein means a process or method by which the size of a population of particles is reduced.

As used herein, the term "micron" or "μm" refers to "micrometer" which is $1 \times 10^{-6}$ meter.

As used herein, "crystalline particles" means any combination of single crystals, aggregates and agglomerates.

As used herein, "Particle Size Distribution (P.S.D)" means the cumulative volume size distribution of equivalent spherical diameters as determined by laser diffraction in Malvern Master Sizer 2000 equipment or its equivalent.

As used herein, $D_X$ means that X percent of the particles have a diameter less than a specified diameter D. Thus, a $D_{90}$ or d(0.9) of less than 300 microns means that 90 volume-percent of the particles in a composition have a diameter less than 300 microns.

By "substantially pure" is meant having purity greater than about 98%, specifically greater than about 99%, and more specifically greater than about 99.9% measured by HPLC.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The term wt % refers to percent by weight. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. Laquinimod sodium as being greater than 98% pure:
   a) in a crystalline Form A1;
   b) in a crystalline Form A3; or
   c) in a crystalline Form A4;
   wherein:
   e) the crystalline Form A1 has one or more of the following properties:
      i) a powder X-ray diffraction pattern substantially in accordance with FIG. 4;
      ii) a powder X-ray diffraction pattern having peaks at about 9.1, 10.7 and 11.2±0.2 degrees 2-theta;
      iii) a powder X-ray diffraction pattern having additional peaks at about 7.25, 9.72, 10.03, 13.08, 13.91, 14.57, 14.99, 15.69, 16.12, 16.75, 17.57, 18.15, 19.16, 19.87, 20.44, 21.24, 21.68, 21.88, 22.98, 23.79, 24.63 and 25.63±0.2 degrees 2-theta;
      iv) an IR spectrum substantially in accordance with FIG. 5;
      v) an IR spectrum having absorption bands at about 3377, 3062, 2972, 2933, 1611, 1585, 1528, 1495, 1414, 1377, 1347, 1325, 1255, 1220, 1178, 1098, 811 and 697±2 $cm^{-1}$; and
      vi) a DSC thermogram substantially in accordance with FIG. 6;
   f) the crystalline Form A3 has one or more of the following properties:
      i) a powder X-ray diffraction pattern substantially in accordance with FIG. 10;
      ii) a powder X-ray diffraction pattern having peaks at about 6.44, 6.65, 7.72 and 8.77±0.2 degrees 2-theta;
      iii) a powder X-ray diffraction pattern having additional peaks at about 9.31, 9.60, 10.71, 11.14, 11.66, 13.25, 14.61, 15.32, 17.62, 17.98, 18.54, 19.21, 21.38, 22.11, 22.59, 23.43, 23.99, 25.04, 25.44 and 27.86±0.2 degrees 2-theta;
      iv) an IR spectrum substantially in accordance with FIG. 11;
      v) an IR spectrum having absorption bands at about 3368, 2970, 2936, 1615, 1583, 1526, 1495, 1412, 1377, 1344, 1326, 1253, 1218, 1177, 1097, 813 and 699±2 $cm^{-1}$; and
      vi) a DSC thermogram substantially in accordance with FIG. 12;
   g) the crystalline Form A4 has one or more of the following properties:
      i) a powder X-ray diffraction pattern substantially in accordance with FIG. 13;
      ii) a powder X-ray diffraction pattern having peaks at about 6.09, 7.46 and 10.42±0.2 degrees 2-theta;
      iii) a powder X-ray diffraction pattern having additional peaks at about 7.82, 8.47, 10.12, 14.15, 16.10, 18.95, 22.66, 23.50, 25.84, 26.13, 28.24, 29.07, 29.81, 31.62 and 33.94±0.2 degrees 2-theta;

iv) an IR spectrum substantially in accordance with FIG. 14;

v) an IR spectrum having absorption bands at about 3413, 2974, 2935, 1612, 1584, 1524, 1495, 1413, 1377, 1346, 1327, 1253, 1219, 1177, 1097, 811 and 698±2 cm$^{-1}$; and vi) a DSC thermogram substantially in accordance with FIG. 15.

2. A process for the preparation of laquinimod sodium crystalline Form A1 of claim 1, comprising:

a) providing a solution of laquinimod sodium in an alcoholic solvent;

b) optionally, filtering the solvent solution to remove any extraneous matter;

c) optionally, seeding the solution;

d) stirring the solution at about 15-30° C. for at least 1 hour to form a first reaction mass;

e) cooling the first reaction mass at below about 10° C. to form a second reaction mass; and f) recovering the crystalline Form A1 of laquinimod sodium from the second reaction mass.

3. The process of claim 2, wherein the alcohol solvent used in step-(a) is selected from the group consisting of methanol, ethanol, isopropyl alcohol, butanol, amyl alcohol, hexanol, and mixtures thereof; wherein the solution obtained in step-(a) is optionally subjected to carbon treatment or silica get treatment; wherein the solution in step-(d) is stirred for about 2 hours to about 6 hours at a temperature of about 20° C. to about 30° C.; wherein the solution in step-(e) is stirred at a temperature of about 0-5° C. for about 30 minutes to about 4 hours; and wherein recovering in step-(f) is carried out by filtration, filtration under vacuum, decantation, centrifugation, filtration employing a filtration media of a silica gel or celite, or a combination thereof.

4. The process of claim 3, wherein the alcohol solvent is ethanol.

5. A process for the preparation of laquinimod sodium crystalline Form A3 of claim 1, comprising:

a) providing a solution of laquinimod sodium in an alcoholic solvent;

b) optionally, filtering the solvent solution to remove any extraneous matter;

c) optionally, seeding the solution;

d) admixing the solution with an anti-solvent, wherein the anti-solvent is selected from the group consisting of an ether, a hydrocarbon, and mixtures thereof; and e) recovering the crystalline Form A3 of laquinimod sodium from the reaction mass obtained in step-(d).

6. The process of claim 5, wherein the alcohol solvent used in step-(a) is selected from the group consisting of methanol, ethanol, isopropyl alcohol, butanol, amyl alcohol, hexanol, and mixtures thereof; wherein the solution obtained in step-(a) is optionally subjected to carbon treatment or silica get treatment; wherein the anti-solvent used in step-(d) is selected from the group consisting of diisopropyl ether, diethyl ether, tetrahydrofuran, dioxane, n-pentane, n-hexane and n-heptane and their isomers, cyclohexane, toluene, xylene, and mixtures thereof; and wherein recovering in step-(e) is carried out by filtration, filtration under vacuum, decantation, centrifugation, filtration employing a filtration media of a silica gel or celite, or a combination thereof.

7. The process of claim 6, wherein the alcohol solvent used in step-(a) is ethanol; and wherein the anti-solvent is diisopropyl ether.

8. A process for the preparation of laquinimod sodium crystalline Form A4 of claim 1, comprising:

a) providing a solution of laquinimod sodium in a ketone solvent;

b) optionally, filtering the solvent solution to remove any extraneous matter;

c) optionally, seeding the solution; and d) isolating crystalline Form A4 of laquinimod sodium from the solution.

9. The process of claim 8, wherein the ketone solvent used in step-(a) is selected from the group consisting of acetone, methyl ethyl ketone, methyl isobutyl ketone, methyl tert-butyl ketone, and mixtures thereof; wherein the solution obtained in step-(a) is optionally subjected to carbon treatment or silica get treatment; wherein the isolation of laquinimod sodium crystalline Form A4 in step-(d) is carried out by cooling, seeding, partial removal of the solvent from the solution, by adding an anti-solvent to the solution, or a combination thereof; and wherein the solid obtained in step-(d) is recovered by filtration, filtration under vacuum, decantation, centrifugation, filtration employing a filtration media of a silica gel or celite, or a combination thereof.

10. The process of claim 9, wherein the ketone solvent is acetone and wherein the isolation in step-(d) is carried out at about 0° C. to about 25° C.

11. A process for the preparation of crystalline Form A2 of laquinimod sodium, comprising:

a) providing a solution of laquinimod sodium in an alcoholic solvent, wherein the alcohol solvent is selected from the group consisting of methanol, ethanol, isopropyl alcohol and mixtures thereof;

b) optionally, filtering the solvent solution to remove any extraneous matter;

c) optionally, seeding the solution;

d) stirring the solution at a temperature of about 25° C. to about 30° C. for about 6 hours to about 30 hours to produce a reaction mass; and e) recovering the crystalline Form A2 of laquinimod sodium from the reaction mass obtained in step-(d);

wherein the laquinimod sodium crystalline Form A2 is characterized by one or more of the following properties:

i) a powder X-ray diffraction pattern substantially in accordance with FIG. 7;

ii) a powder X-ray diffraction pattern having peaks at about 8.36, 25.10 and 29.35±0.2 degrees 2-theta;

iii) a powder X-ray diffraction pattern having additional peaks at about 7.22, 9.68, 10.00, 11.79, 13.37, 13.78, 14.08, 14.31, 14.62, 15.02, 15.73, 16.14, 16.74, 17.82, 18.20, 18.90, 20.07, 22.09, 23.17 and 24.08±0.2 degrees 2-theta;

iv) an IR spectrum substantially in accordance with FIG. 8;

v) an IR spectrum having absorption bands at about 3301, 2971, 2935, 1613, 1585, 1526, 1495, 1414, 1378, 1347, 1328, 1253, 1220, 1178, 1098, 811 and 700±2 cm$^{-1}$; and vi) a DSC thermogram substantially in accordance with FIG. 9.

12. A crystalline Form A of laquinimod acid characterized by at least one, or more, of the following properties:

i) a powder X-ray diffraction pattern substantially in accordance with FIG. 1;

ii) a powder X-ray diffraction pattern having peaks at about 7.15, 12.58, 14.84, 25.09 and 26.38±0.2 degrees 2-theta;

iii) a powder X-ray diffraction pattern having additional peaks at about 6.19, 8.78, 14.04, 14.37, 15.36, 16.20, 18.48, 18.81, 20.44, 20.73, 21.71, 23.21, 23.50, 23.76, 28.96 and 31.08±0.2 degrees 2-theta;

iv) an IR spectrum substantially in accordance with FIG. 2;
v) an IR spectrum having absorption bands at about 3081, 2976, 1647, 1617, 1586, 1562, 1496, 1378, 1327, 1303, 1237, 1197, 812 and 701±2 cm$^{-1}$ and
vi) a DSC thermogram having an endotherm peak at about 240° C. substantially as depicted in FIG. 3.

13. A process for the preparation of laquinimod crystalline Form A of claim 12, comprising:
   a) providing a suspension of N-ethyl-N-phenyl-1,2-dihydro-4-hydroxy-5-chloro-1-methyl-2-oxoquinoline-3-carboxamide (laquinimod or laquinimod acid) in a solvent medium comprising an ester solvent and a halogenated hydrocarbon solvent;
   b) optionally, cooling the suspension obtained in step-(a); and
   c) recovering crystalline Form A of laquinimod from the suspension;
   wherein the halogenated hydrocarbon solvent is selected from the group consisting of methylene chloride, 1,2-dichloroethane, chloroform, carbon tetrachloride, and mixtures thereof; and wherein the ester solvent is selected from the group consisting of methyl acetate, ethyl acetate, n-propyl acetate, isopropyl acetate, n-butyl acetate, isobutyl acetate, tert-butyl acetate, ethyl formate, and mixtures thereof.

14. A pharmaceutical composition comprising a therapeutically effective amount of laquinimod crystalline Form A of claim 12, and one or more pharmaceutically acceptable excipients.

15. A pharmaceutical composition comprising a therapeutically effective amount of any one or a mixture of the laquinimod sodium solid state forms (Form A1, Form A3 and Form A4 and amorphous form) of claim 1, and one or more pharmaceutically acceptable excipients.

16. The pharmaceutical composition of claim 15, wherein the solid state form of laquinimod sodium has a $D_{90}$ particle size of less than or equal to about 500 microns.

17. The pharmaceutical composition of claim 16, wherein the solid state form of laquinimod sodium has a $D_{90}$ particle size of less than or equal to about 300 microns; less than or equal to about 100 microns; less than or equal to about 60 microns; or less than or equal to about 15 microns.

18. A method for treating a patient suffering from diseases caused by multiple sclerosis, insulin-dependent diabetes mellitus, systemic lupus erythematosus, rheumatoid arthritis, inflammatory bowel disease and psoriasis, asthma, atherosclerosis, stroke and Alzheimer's disease; comprising administering any one or a mixture of the solid state forms of laquinimod sodium (Form A1, Form A3 and Form A4 and amorphous form) of claim 1, or a pharmaceutical composition that comprises any one or a mixture of the solid state forms of laquinimod sodium along with pharmaceutically acceptable excipients.

* * * * *

UNITED STATES PATENT AND TRADEMARK OFFICE
CERTIFICATE OF CORRECTION

PATENT NO. : 8,354,428 B2  
APPLICATION NO. : 13/001715  
DATED : January 15, 2013  
INVENTOR(S) : Girish Dixit et al.

Page 1 of 1

It is certified that error appears in the above-identified patent and that said Letters Patent is hereby corrected as shown below:

In the Specifications

In column 2, line 43, delete "and for" and insert -- and/or --, therefor.

In column 7, line 33, delete "Rotocon" and insert -- Rotocone --, therefor.

In column 18, line 26, delete "2θ;" and insert -- 2θ; --, therefor.

In column 23, line 33, delete "Master Sizer" and insert -- MasterSizer --, therefor.

In the Claims

In column 26, line 22, in Claim 10, delete "acetone" and insert -- acetone; --, therefor.

In column 27, line 4, in Claim 12, delete "2 cm$^{-1}$" and insert -- 2 cm$^{-1}$; --, therefor.

In column 28, line 4, in Claim 15, after "Form A4" delete "and amorphous form".

In column 28, lines 21-22, in Claim 18, after "Form A4" delete "and amorphous form".

Signed and Sealed this  
Thirtieth Day of July, 2013

Teresa Stanek Rea  
*Acting Director of the United States Patent and Trademark Office*